(12) United States Patent
Bays et al.

(10) Patent No.: US 6,610,665 B1
(45) Date of Patent: Aug. 26, 2003

(54) 2-(PURIN-9-YL)-TETRAHYDROFURAN-3, 4-DIOL DERIVATIVES

(75) Inventors: David Edmund Bays, Ware (GB); Chuen Chan, Stevenage (GB); Caroline Mary Cook, Stevenage (GB); Brian Cox, Stevenage (GB); Richard Peter Charles Cousins, Stevenage (GB); Hazel Joan Dyke, Cambridge (GB); Frank Ellis, Stevenage (GB); Joanna Victoria Geden, Birmingham (GB); Stephen Swanson, Stevenage (GB)

(73) Assignee: Smithkline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/622,313
(22) PCT Filed: Feb. 12, 1999
(86) PCT No.: PCT/EP99/00915
§ 371 (c)(1), (2), (4) Date: Aug. 29, 2000
(87) PCT Pub. No.: WO99/41267
PCT Pub. Date: Aug. 19, 1999

(30) Foreign Application Priority Data

Feb. 14, 1998 (GB) .............................................. 9803169
Jun. 23, 2000 (GB) .............................................. 9813533

(51) Int. Cl.$^7$ ....................... A61K 31/70; C07H 19/167
(52) U.S. Cl. ...................... 514/46; 536/27.23
(58) Field of Search ........................ 514/46; 536/27.23

(56) References Cited

U.S. PATENT DOCUMENTS 6,426,337 B1 * 7/2002 Cox et al. ...................... 514/45
6,495,528 B1 * 12/2002 Allen et al. ................... 514/46

FOREIGN PATENT DOCUMENTS

| WO | 96 02553 A | 2/1996 |
| WO | 98 28319 | 7/1998 |
| WO | W O 99/41267 A1 * | 8/1999 |
| WO | WO 99/41267 A1 * | 8/1999 |

OTHER PUBLICATIONS

Kobe et al., "Preparation and Utility of 5–β–D–Ribofuranosyl–1H–tetrazole as a Key Synthon for C–Nucleoside Synthesis," *Nucleoside & Nucleotides*, 13(10), 2209–2244 (1994).*

Hennen, William J. et al: "Synthesis of 5–(.beta–D–ribofuranosyl)–1,2,4–oxadiazole–3–3caroxamide" J. Heterocycl. Chem. (1985), 22(6), 1747–8, XP002107414 see p. 1747, left–hand column, paragraph 1 see page 1747, left–hand column, last paragraph (Nov.–Dec., 1985).

* cited by examiner

*Primary Examiner*—James O. Wilson
*Assistant Examiner*—L E Crane
(74) *Attorney, Agent, or Firm*—Nixon & Vanderhye P.C.

(57) ABSTRACT

There are disclosed according to the invention, compounds of formula (I) wherein $R^1$, $R^2$ and $R^3$ are defined in the specification. Additionally, processes of preparing the compounds of formula (I), formulations containing same, and the administration of said compounds or formulations thereof in the treatment of inflammatory diseases are also disclosed.

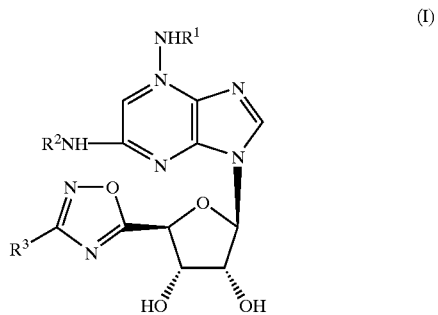

27 Claims, No Drawings

2-(PURIN-9-YL)-TETRAHYDROFURAN-3,4-DIOL DERIVATIVES

This is a 371 of PCT/EP99/00915, filed Feb. 12, 1999.

This invention relates to new chemical compounds, processes for their preparation, pharmaceutical formulations containing them and their use in therapy.

Inflammation is a primary response to tissue injury or microbial invasion and is characterised by leukocyte adhesion to the endothelium, diapedesis and activation within the tissue. Leukocyte activation can result in the generation of toxic oxygen species (such as superoxide anion), and the release of granule products (such as peroxidases and proteases). Circulating leukocytes include neutrophils, eosinophils, basophils, monocytes and lymphocytes. Different forms of inflammation involve different types of infiltrating leukocytes, the particular profile being regulated by the profile of adhesion molecule, cytokine and chemotactic factor expression within the tissue.

The primary function of leukocytes is to defend the host from invading organisms such as bacteria and parasites. Once a tissue is injured or infected a series of events occurs which causes the local recruitment of leukocytes from the circulation into the affected tissue. Leukocyte recruitment is controlled to allow for the orderly destruction and phagocytosis of foreign or dead cells, followed by tissue repair and resolution of the inflammatory infiltrate. However in chronic inflammatory states, recruitment is often inappropriate, resolution is not adequately controlled and the inflammatory reaction causes tissue destruction.

There is evidence from both in vitro and in vivo studies to suggest that compounds active at the adenosine A2a receptor will have anti-inflammatory actions. The area has been reviewed by Cronstein (1994). Studies on isolated neutrophils show an A2 receptor-mediated inhibition of superoxide generation, degranulation, aggregation and adherence (Cronstein et al, 1983 and 1985; Burkey and Webster, 1993; Richter, 1992; Skubitz et al, 1988. When agents selective for the A2a receptor over the A2b receptor (eg CGS21680) have been used, the profile of inhibition appears consistent with an action on the A2a receptor subtype (Dianzani et al, 1994). Adenosine agonists may also down-regulate other classes of leukocytes (Elliot and Leonard, 1989; Peachell et al, 1989). Studies on whole animals have shown the anti-inflammatory effects of methotrexate to be mediated through adenosine and A2 receptor activation (Asako et al, 1993; Cronstein et al, 1993 and 1994). Adenosine itself, and compounds that raise circulating levels of adenosine also show anti-inflammatory effects in vivo (Green et al, 1991; Rosengren et al, 1995). In addition raised levels of circulating adenosine in man (as a result of adenosine deaminase deficiency) results in immunosuppression (Hirschorn, 1993).

We have now found a novel group of compounds with broad anti-inflammatory properties which inhibit leukocyte recruitment and activation and which are agonists of the adenosine 2a receptor. The compounds are therefore of potential therapeutic benefit in providing protection from leukocyte-induced tissue damage in diseases where leukocytes are implicated at the site of inflammation. The compounds of the invention may also represent a safer alternative to corticosteroids in the treatment of inflammatory diseases, whose uses are severely limited by their side-effect profiles.

More particularly, the compounds of this invention may show an improved profile over known A2a-selective agonists in that they generally lack agonist activity at the human A3 receptor. They may even possess antagonist activity at the human A3 receptor. This profile can be considered of benefit as A3 receptors are also found on leukocytes (eg eosinophil) and other inflammatory cells (eg mast cell) and activation of these receptors may have pro-inflammatory effects (Kohno et al, 1996; Van Schaick et al 1996). It is even considered that the bronchoconstrictor effects of adenosine in asthmatics may be mediated via the adenosine A3 receptor (Kohno et al, 1996).

Thus, according to the invention we provide compounds of formula (I):

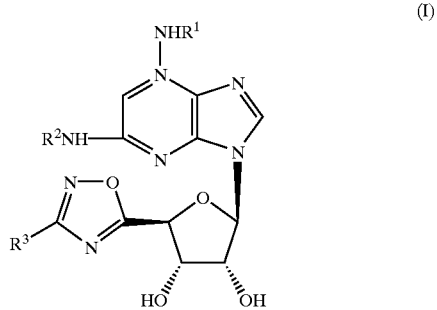

(I)

wherein $R^1$ and $R^2$ independently represent a group selected from:

(i) $C_{3-8}$cycloalkyl-;
(ii) hydrogen;
(iii) aryl$_2$CHCH$_2$—;
(iv) $C_{3-8}$cycloalkyl$C_{1-6}$alkyl-;
(v) $C_{1-8}$alkyl-;
(vi) aryl$C_{1-6}$alkyl-;
(vii) $R^4R^5N$—$C_{1-6}$alkyl-;
(viii) $C_{1-6}$alkyl-CH(CH$_2$OH)—;
(ix) aryl$C_{1-5}$alkyl-CH(CH$_2$OH)—;
(x) aryl$C_{1-5}$alkyl-C(CH$_2$OH)$_2$—;
(xi) $C_{3-8}$cycloalkyl independently substituted by one or more (e.g. 1, 2 or 3) —(CH$_2$)$_p$R$^6$ groups;
(xii) H$_2$NC(=NH)NHC$_{1-6}$alkyl-;
(xiii) a group of formula

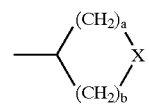

or such a group in which one methylene carbon atom adjacent to X, or both if such exist, is substituted by methyl;
(xiv) —$C_{1-6}$alkyl-OH;
(xv) —$C_{1-8}$haloalkyl;
(xvi) a group of formula

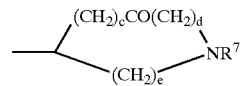

(xvii) aryl; and
(xviii) —(CH$_2$)$_f$SO$_2$NH$_g$(C$_{1-4}$alkyl-)$_{2-g}$ or —(CH$_2$)$_f$SO$_2$NH$_g$(arylC$_{1-4}$alkyl-)$_{2-g}$;

$R^3$ represents methyl, ethyl, —CH=CH$_2$, n-propyl, —CH$_2$CH=CH$_2$, —CH=CHCH$_3$, isopropenyl, cyclopropyl, cyclopropenyl, —CH(OH)CH$_3$, —(CH$_2$)$_q$halogen, —(CH$_2$)$_h$Y(CH$_2$)$_i$H, —COO(CH$_2$)$_j$H, —CON(CH$_2$)$_m$H((CH$_2$)$_n$H), —CO(CH$_2$)$_o$H, or —C((CH$_2$)$_u$H)=NO(CH$_2$)$_v$H;

Y represents O, S or N(CH$_2$)$_j$H;

a and b independently represent an integer 0 to 4 provided that a+b is in the range 3 to 5;

c, d and e independently represent an integer 0 to 3 provided that c+d+e is in the range 2 to 3;

f represents 2 or 3 and g represents an integer 0 to 2;

p represents 0 or 1;

q represents 1 or 2;

h represents 1 or 2 and i represents an integer 0 to 1; such that h+i is in the range 1 to 2;

j represents an integer 0 to 1 such that h+i+j is in the range 1 to 2;

l represents 1 or 2;

m and n independently represent an integer 0 to 2 such that m+n is in the range 0 to 2;

o represents an integer 0 to 2;

u and v independently represent 0 or 1 such that u+v is in the range 0 to 1;

R$^4$ and R$^5$ independently represent hydrogen, C$_{1-6}$alkyl, aryl, arylC$_{1-6}$alkyl- or NR$^4$R$^5$ together may represent pyridinyl, pyrrolidinyl, piperidinyl, morpholinyl, azetidinyl, azepinyl, piperazinyl or N—C$_{1-6}$alkylpiperazinyl;

R$^6$ represents OH, NH$_2$, NHCOCH$_3$ or halogen;

R$^7$ represents hydrogen, C$_{1-6}$alkyl, —C$_{1-6}$alkylaryl or —COC$_{1-6}$alkyl;

X represents NR$^7$, O, S, SO or SO$_2$;

and salts and solvates thereof.

References to C$_{x-y}$alkyl include references to an aliphatic hydrocarbon grouping containing x to y carbon atoms which may be straight chain or branched and may be saturated or unsaturated. References to alkoxy may also be interpreted similarly. Preferably these groups will be saturated.

References to aryl include references to mono- and bicyclic carbocyclic aromatic rings (e.g. phenyl, naphthyl) and heterocyclic aromatic rings, for example containing 1–3 hetero atoms selected from N, O and S (e.g. pyridinyl, pyrimidinyl, thiophenyl, imidazolyl, quinolinyl, furanyl, pyrrolyl, oxazolyl) all of which may be optionally substituted, e.g. by C$_{1-6}$alkyl, halogen, hydroxy, nitro, C$_{1-6}$alkoxy, cyano, amino, SO$_2$NH$_2$ or —CH$_2$OH.

Examples of C$_{3-8}$cycloalkyl for R$^1$ and R$^2$ include monocyclic alkyl groups (e.g. cyclopentyl, cyclohexyl) and bicyclic alkyl groups (e.g. norbornyl such as exo-norborn-2-yl).

Examples of (aryl)$_2$CHCH$_2$— for R$^1$ and R$^2$ include Ph$_2$CHCH$_2$— or such a group in which one or both phenyl moieties is substituted, e.g. by halogen or C$_{1-4}$alkyl.

Examples of C$_{3-8}$cycloalkylC$_{1-6}$alkyl- for R$^1$ and R$^2$ include ethylcyclohexyl.

Examples of C$_{1-8}$alkyl for R$^1$ and R$^2$ include —(CH$_2$)$_2$C(Me)$_3$, —CH(Et)$_2$ and CH$_2$=C(Me)CH$_2$CH$_2$—.

Examples of arylC$_{1-6}$alkyl- for R$^1$ and R$^2$ include —(CH$_2$)$_2$Ph, —CH$_2$Ph or either in which Ph is substituted (one or more times) by halogen (e.g. iodine), amino, methoxy, hydroxy, —CH$_2$OH or SO$_2$NH$_2$; —(CH$_2$)$_2$ pyridinyl (e.g. —CH$_2$pyridin-2-yl) optionally substituted by amino; (CH$_2$)$_2$imidazolyl (e.g. 1H-imidazol-4-yl) or this group in which imidazole is N-substituted by C$_{1-6}$alkyl (especially methyl).

Examples of R$^4$R$^5$N—C$_{1-6}$alkyl- for R$^1$ and R$^2$ include ethyl-piperidin-1-yl, ethyl-pyrrolidin-1-yl, ethyl-morpholin-1-yl, —(CH$_2$)$_2$NH(pyridin-2-yl) and —(CH$_2$)$_2$NH$_2$.

Examples of C$_{1-6}$alkyl-CH(CH$_2$OH)— for R$^1$ and R$^2$ include Me$_2$CHCH(CH$_2$OH)—.

Examples of arylC$_{1-5}$alkyl-CH(CH$_2$OH)— for R$^1$ and R$^2$ include PhCH$_2$CH(CH$_2$OH)— particularly

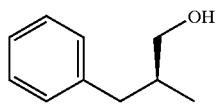

Examples of arylC$_{1-5}$alkyl-C(CH$_2$OH)$_2$— for R$^1$ and R$^2$ include PhCH$_2$C(CH$_2$OH)$_2$—.

Examples of C$_{3-8}$ cycloalkyl independently substituted by one or more —(CH$_2$)$_p$R$^6$ groups (eg 1, 2 or 3 such groups) for R$^1$ and R$^2$ include 2-hydroxy-cyclopentyl (especially trans- 2-hydroxy-cyclopentyl) and 4-aminocyclohexyl (especially trans-4-amino-cyclohexyl).

Examples of H$_2$NC(=NH)NHC$_{1-6}$alkyl for R$^1$ and R$^2$ include H$_2$NC(=NH)NH(CH$_2$)$_2$—

Examples of groups of formula

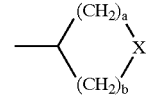

for R$^1$ and R$^2$ include pyrrolidin-3yl, piperidin-3-yl, piperidin-4-yl, tetrahydro-1,1-dioxide thiophen-3-yl, tetrahydropyran-4-yl, tetrahydrothiopyran-4-yl and 1,1-dioxo-hexahydro-1.lamda.6-thiopyran-4-yl, or a derivative in which the ring nitrogen is substituted by C$_{1-6}$alkyl (e.g. methyl), C$_{1-6}$alkylacyl (e.g. acetyl), arylC$_{1-6}$alkyl- (e.g. benzyl).

Examples of —C$_{1-6}$alkyl-OH groups for R$^1$ and R$^2$ include —CH$_2$CH$_2$OH and —CH(CH$_2$OH)CH(CH$_3$)$_2$.

Examples of C$_{1-8}$haloalkyl for R$^1$ and R$^2$ include —CH$_2$CH$_2$Cl and (CH$_3$)$_2$ClC(CH$_2$)$_3$—.

Examples of groups of formula

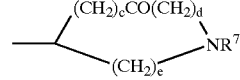

for R$^1$ and R$^2$ include 2-oxopyrrolidin-4-yl, 2-oxopyrrolidin-3-yl or a derivative in which the ring nitrogen is substituted by C$_{1-6}$alkyl (e.g. methyl) or benzyl.

Examples of aryl for R$^1$ and R$^2$ include phenyl optionally substituted by halogen (e.g. fluorine, especially 4-fluorine).

An example of a —(CH$_2$)$_f$SO$_2$NH$_g$(C$_{1-4}$alkyl)$_{2-g}$ group for R$^1$ and R$^2$ is —(CH$_2$)$_2$SO$_2$NHMe, and an example of a —(CH$_2$)$_f$SO$_2$NH$_g$(arylC$_{1-4}$alkyl)$_{2-g}$ group for R$^1$ and R$^2$ is —(CH$_2$)$_2$SO$_2$NHCH$_2$Ph.

An example of C$_{1-6}$alkyl for R$^7$ is methyl, an example of C$_{1-6}$alkylaryl for R$^7$ is benzyl, and an example of —COC$_{1-6}$ alkyl for R$^7$ is acetyl.

We prefer that R$^1$ and R$^2$ do not both represent hydrogen.

We prefer R$^1$ to represent aryl$_2$CHCH$_2$—.

We also prefer R$^1$ to represent C$_{1-8}$alkyl, C$_{3-8}$cycloalkylC$_{1-6}$alkyl-, arylC$_{1-6}$alkyl- or hydrogen.

We prefer R$^2$ to represent —CH(CH$_2$OH)C$_{1-3}$alkyl, 4-aminocyclohexyl, pyrrolidinyl (particularly pyrrolidin-3-yl) or arylCH$_2$CH$_2$—, especially where aryl represents (1-C$_{1-3}$alkyl-1H-imidazol-4-yl).

We also prefer R$^2$ to represent pyrrolidin-3-yl N-substituted by C$_{1-6}$alkyl or benzyl, R$^4$R$^5$NC$_{1-6}$alkyl, C$_{1-6}$alkyl-OH, aryl (especially where aryl represents phenyl substituted by halogen), arylC$_{1-5}$alkyl-CH(CH$_2$OH)—, C$_{3-8}$cycloalkyl, aryl(CH$_2$)$_2$ (especially where aryl represents pyridinyl (particularly pyridin-2-yl), 1H-imidazol-4-yl, phenyl or phenyl disubstituted by methoxy) or C$_{3-8}$cycloalkyl independently substituted by one or more (e.g. 1, 2 or 3) —(CH$_2$)$_p$R$^6$ groups.

We prefer R$^3$ to represent methyl, ethyl, n-propyl, cyclopropyl, —CH$_2$OH, —COOCH$_3$ or —CH═NOH, more preferably methyl, ethyl, n-propyl, cyclopropyl or —CH$_2$OH.

We particularly prefer R$^3$ to represent methyl, ethyl, n-propyl or cyclopropyl, most particularly methyl, ethyl or cyclopropyl, especially methyl or ethyl, most especially ethyl.

We prefer R$^4$ and R$^5$ independently to represent hydrogen, C$_{1-6}$alkyl, aryl, arylC$_{1-6}$alkyl- or NR$^4$R$^5$ together may represent pyrrolidinyl, piperidinyl, morpholinyl, azetidinyl, azepinyl, piperazinyl or N—C$_{1-6}$alkylpiperazinyl;

We particularly prefer R$^4$ and R$^5$ independently to represent hydrogen or aryl or NR$^4$R$^5$ together to represent pyrrolidinyl, piperidinyl, morpholinyl, azetidinyl, azepinyl, piperazinyl or N-methylpiperazinyl.

We prefer that p represents 0. We prefer that R$^6$ represents OH or NH$_2$.

We prefer q to represent 1. We prefer h to represent 1. We prefer i to represent 0. We prefer j to represent 1. We prefer l to represent 1. We prefer m and n to represent 0. We prefer o to represent 1. We prefer u to represent 0. We prefer v to represent 0. We prefer Y to represent O.

We prefer that a represents 2 and that b represents 1 or 2. We prefer X to represent NR$^7$ (e.g. NH), O, S or SO$_2$, particularly O, S or NH.

We prefer that c represents 0, and either that d represents 1 and e represents 1 or d represents 0 and e represents 2. We prefer that R$^7$ represents hydrogen.

We particularly prefer R$^1$ to represent Ph$_2$CHCH$_2$—.

We also particularly prefer R$^1$ to represent CH(CH$_2$CH$_3$)$_2$, phenylethyl, cyclohexylethyl, —(CH$_2$)$_2$C(CH$_3$)$_3$ or hydrogen.

We particularly prefer R$^2$ to represent —CH(CH$_2$OH)CH(CH$_3$)$_2$ (particularly 1S-hydroxymethyl-2-methyl-propyl), trans4-amino-cyclohexyl, 2-(1-methyl-1H-imidazol-4-yl)CH$_2$CH$_2$— or pyrrolidin-3-yl.

We also particularly prefer R$^2$ to represent 2-(1H-imidazol-4-yl) ethyl, morpholin-1-ylethyl, pyrrolidin-1-ylethyl, pyridin-2-ylaminoethyl, (+)-exonorborn-2-yl, 3,4-dimethoxy phenylethyl, 2-hydroxyethyl, 4-fluorophenyl, N-benzyl-pyrrolidin-3-yl, pyridin-2ylethyl, 1S-hydroxymethyl-2-phenylethyl, cyclopentyl, phenylethyl, piperidin-1-ylethyl or 2-hydroxypentyl (particularly trans-2-hydroxypentyl).

We especially prefer R$^1$ to represent Ph$_2$CHCH$_2$—, —CH(CH$_2$CH$_3$)$_2$, hydrogen or phenylethyl-.

We especially prefer R$^2$ to represent 2-(1-methyl-1H-imidazol-4-yl)CH$_2$CH$_2$—, 1S-hydroxymethyl-2-phenylethyl, phenylethyl or 1S-hydroxymethyl-2-methyl-propyl.

The most preferred compounds of formula (I) are
(2R,3R,4S,5S)-2-{6-(2,2-Diphenyl-ethylamino)-2-[2-(1-methyl-1H-imidazol-4-yl)-ethylamino]-purin-9-yl}-5-(3-ethyl-[1,2,4]oxadiazol-5yl)-tetrahydro-furan-3,4-diol;
(2S,3S,4R,5R)-2-(3-Ethyl-[1,2,4]oxadiazol-5-yl)-5-{6-(1-ethyl-propylamino)-2-[2-(1-methyl-1H-imidazol-4-yl)-ethylamino]-purin-9-yl}-tetrahydro-furan-3,4-diol;
(2R,3R,4S,5S)-2-{6-(1-Ethyl-propylamino)-2-[2-(1-methyl-1H-imidazol-4-yl)-ethylamino]-purin-9-yl}-5-(3-methyl-[1,2,4]oxadiazol-5-yl)-tetrahydro-furan-3,4-diol;
(2R,3R,4S,5S)-2-{6-(2,2-Diphenyl-ethylamino)-2-[2-(1-methyl-1H-imidazol-4-yl)-ethylamino]-purin-9-yl}-5-(3-methyl-[1,2,4]oxadiazol-5-yl)-tetrahydro-furan-3,4-diol;
(2R,3R,4S,5S)-2-{6-Amino-2-[2-(1-methyl-1H-imidazol-4-yl)-ethylamino]-purin-9-yl}-5-(3-methyl-[1,2,4]oxadiazol-5-yl)-tetrahydro-furan-3,4-diol;
(2R,3R,4S,5S)-2-[6Amino-2-(1S-hydroxymethyl-2-phenyl-ethylamino)-purin-9-yl]-5-(3-methyl-[1,2,4]oxadiazol-5-yl)-tetrahydro-furan-3,4-diol;
(2R,3R,4S,5S)-2-(6-Amino-2-phenethylamino-puin-9-yl)-5-(3-methyl-[1,2,4]oxadiazol-5-yl)-tetrahydro-furan-3,4-diol;
(2S,3S,4R,5R)-2-(3-Cyclopropyl-[1,2,4]oxadiazol-5-yl)-5-[6-(1-ethyl-propylamino)-2-(2-(1-methyl-1H-imidazol-4-yl)-ethylamino)-purin-9-yl]-tetrahydrofuran-3,4-diol;
(2R,3R,4S,5S)-2-{6-Phenethylamino-2-[2-(1-methyl-1H-imidazol-4-yl)-ethylamino]-purin-9-yl}-5-(3-ethyl-[1,2,4]oxadiazol-5-yl)-tetrahydro-furan-3,4-diol;
(2R,3R,4S,5S)-2-[6-(2,2-Diphenyl-ethylamino)-2-(1S-hydroxymethyl-2-methyl-propylamino)-punin-9-yl]-5-(3-ethyl-[1,2,4]oxadiazol-5-yl)-tetrahydro-furan-3,4-diol;
(2R,3R,4S,5S)-2-[6-(1-Ethyl-propylamino)-2-(1S-hydroxymethyl-2-phenyl-ethylamino)-purin-9-yl]-5-(3-methyl-[1,2,4]oxadiazol-5-yl)-tetrahydro-furan-3,4-diol;
and salts and solvates thereof.

The representation of formula (I) indicates the absolute stereochemistry. When sidechains contain chiral centres the invention extends to mixtures of enantiomers (including racemic mixtures) and diastereoisomers as well as individual enantiomers. Generally it is preferred to use a compound of formula (I) in the form of a purified single enantiomer.

We also provide a first process for the preparation of compounds of formula (I) including the step of reacting a compound of formula (II)

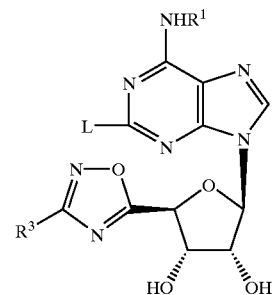

(II)

wherein L represents a leaving group eg halogen, especially chlorine, or a protected derivative thereof;

with a compound of formula R$^2$NH$_2$ or a protected derivative thereof.

Said reaction will generally involve heating the reagents to a temperature of 50° C.–150° C. in the presence of an inert solvent such as DMSO. The compound of formula (II) may be used in a form which the two hydroxyl groups are protected e.g. with acetonide or acetyl groups. Compounds of formula R$^2$NH$_2$ are either known or may be prepared by conventional methods known per se.

Compounds of formula (II) may be prepared from compounds of formula (IV) a first process involving activation of the carboxyl group on the compound of formula (IV) followed by reaction with an amidoxime of formula OH—N═C(R$^3$)NH$_2$ in a solvent such as tetrahydroftran and then cyclisation at temperature of 20° C.–150° C. in a solvent such as toluene. Methods of carboxyl activation include reaction with an acid chloride, such as pivalolyl chloride, or an acid anhydride in the presence of a base such as a tertiary amine, for example di-isopropylethylamine. Activating agents used in peptide chemistry such as EEDQ may also be used. Hydroxyl protecting groups may be removed under conditions know to those practising in the art. For example, the acetonide may be removed by treatment with aqueous acid such as trifluoroacetic acid or acetic acid at a temperature of 0° C.–150° C.

One preferred reaction scheme involving this first process is provided below:

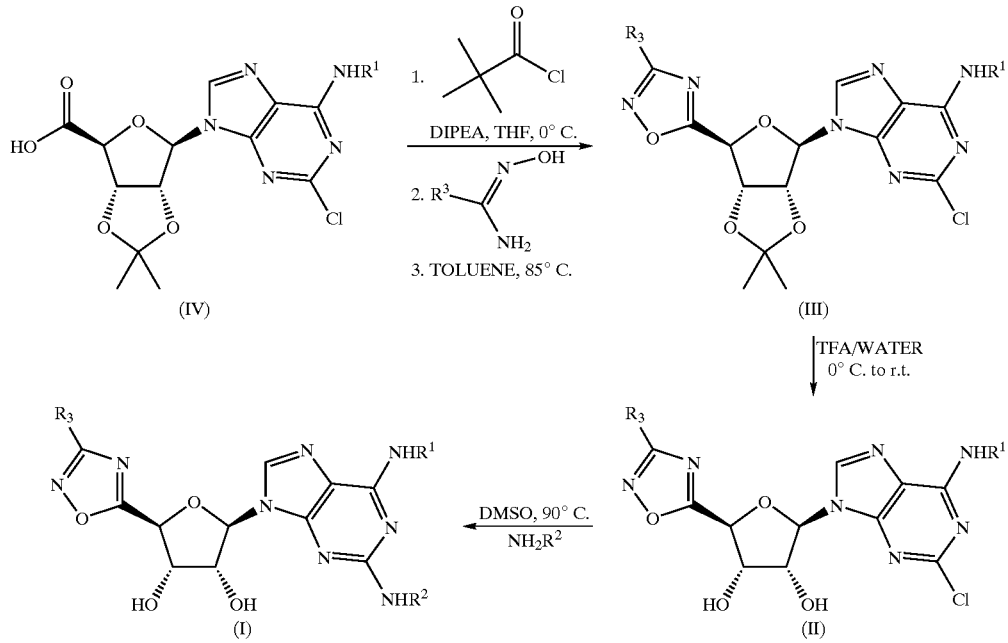

Preferred leaving group L is halogen (particularly chlorine).

The isopropylidine protecting group for the two ribose hydroxy groups in compounds of formula (III) and (IV) are illustrative, and other protecting groups may be contemplated.

Compounds of formula (IV) may be prepared by a method analogous to that described at Preparation 4 ($R^1$ =$Ph_2CHCH_2$—) in International Patent Application No. WO 94/17090 or by processes analogous to those described herein. The synthesis of amidoximes is described in Flora et al, 1978 and Bedford et al, 1986.

Compounds of formula (II) may also be prepared by a process comprising reacting a compound of formula (V)

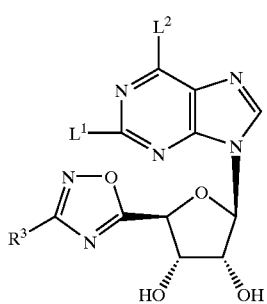

wherein $L^1$ and $L^2$ independently represent a leaving group especially halogen (e.g. chlorine) or a protective derivative thereof with a compound of formula $R^1NH_2$.

This reaction will preferably be performed in the presence of a base such as an amine base (e.g. diisopropylethylamine) in a solvent such as an alcohol (e.g. isopropanol) at elevated temperature (e.g. 50° C.).

We also provide a second process for the preparation of compounds of formula (I) including the step of reacting a compound of formula (VI)

or a protected derivative thereof with a carboxyl activating agent, such as EEDQ, and an amidoxime compound of formula OH—N=C($R^3$)$NH_2$. This reaction may generally be performed at a temperature of 50° C.–150° C. in the presence of an inert solvent such as dioxan.

Compound of formula (VI) may be prepared by oxidation of the hydroxymethyl group of a compound of formula (VII). Suitable methods of oxidation include reaction of the compound of formula (VII) with a permanganate, such as potassium permanganate, in the presence of a base, such as aqueous potassium hydroxide, in an inert water-miscible solvent such as dioxan at a temperature of 0° C.–50° C. Further suitable oxidation methods include the use of TEMPO in the presence of a hypochlorite, such as sodium hypochlorite, and a metal bromide, such as potassium bromide, in the presence of a base, such as sodium hydrogen carbonate, in a biphasic aqueous solvent, such as ethyl acetate, and water at 0° C.–50° C. Other methods of oxidation known to persons skill in the art may also be used.

One preferred reaction scheme involving this second process is provided below:

Scheme 2

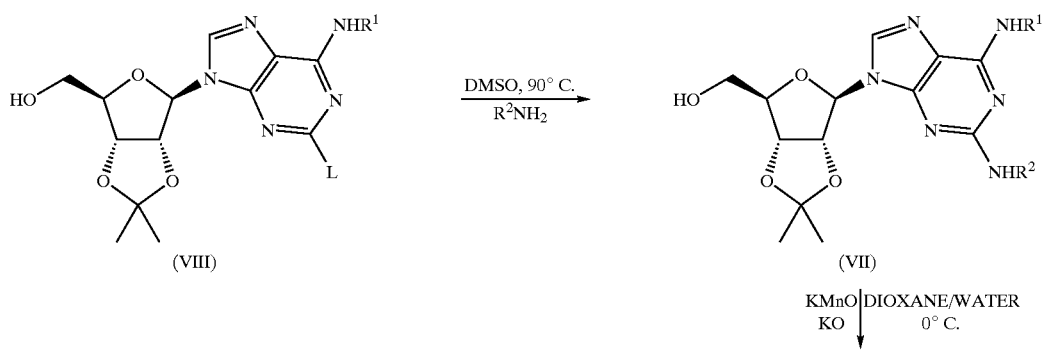

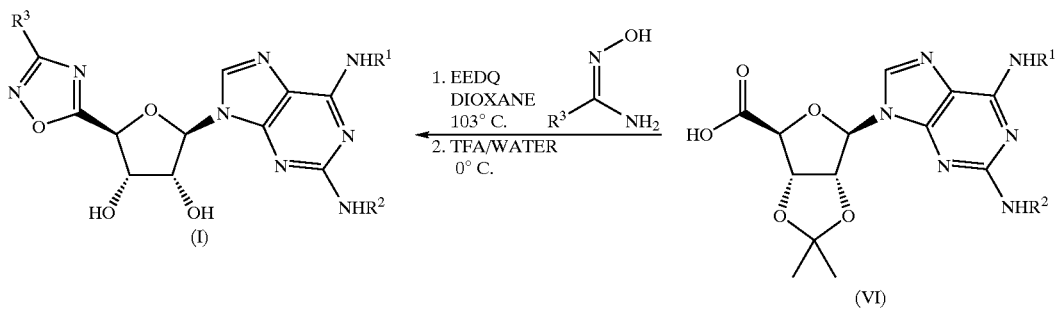

Preferred leaving group L is halogen (particularly chlorine).

Compounds of formula (VII) may be prepared by reacting a compound of formula (VIII) with an amine of formula $R^2NH_2$ in an inert solvent such as DMSO at 50° C.–150° C. Amines of formula $R^2NH_2$ may be obtained commercially or prepared by methods known in the art.

Compounds of formula (VIII) may be prepared by a method analogous to that Oi described at Preparation 3 ($R^1$=$Ph_2CHCH_2$—) in International Patent Application No. WO 94/17090.

We also provide a third process for preparation of compounds of formula I which comprises reacting a compound of formula (IX)

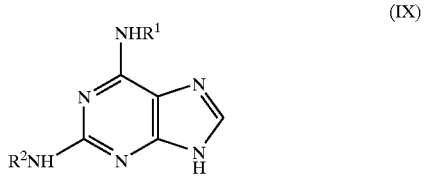

with a compound of formula (X)

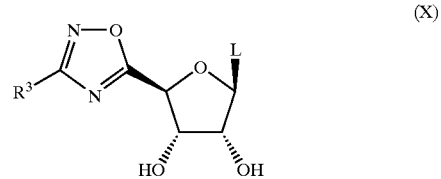

wherein L is a leaving group
or a protected derivative thereof.

We prefer to use the compound of formula (X) when the ribose 2- and 3-hydroxyl groups are protected for example by acetyl. Leaving group L may represent OH but will preferably represent $C_{1-6}$alkoxy (e.g. methoxy or ethoxy) an ester moiety (e.g. acetyloxy or benzoyloxy) or halogen. The preferred group L is acetyloxy. The reaction may be formed by combining the reactants in an inert solvent such as MeCN in the presence of a Lewis Acid (e.g. TMSOTf) and DBU.

This process is also suitable for preparation of compounds of formula (II) in which case a derivative compound of formula (IX) wherein the moiety $R^2NH$ is replaced by L will be used. An analogous process is also suitable for preparation of compounds of formula (V).

Compounds of formula (IX) (and the above mentioned derivatives) are either known or may be prepared by known methods.

For example, compounds of formula (VIII) may be prepared, for example following Scheme 3:

Scheme 3

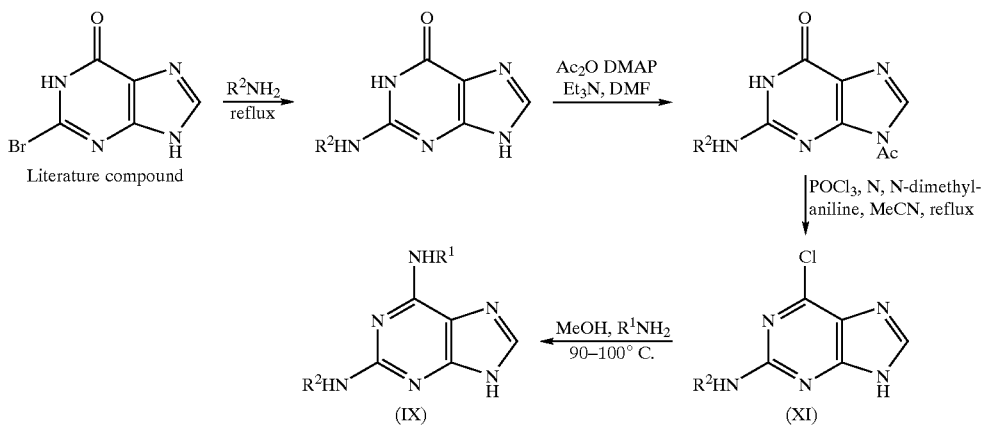

Compounds of formula (X) may be prepared by methods analogous to those described herein for the preparation of compounds of formula (III).

We also provide a fourth process for the preparation of compounds of formula (I) which involves reacting a compound of formula (IIa)

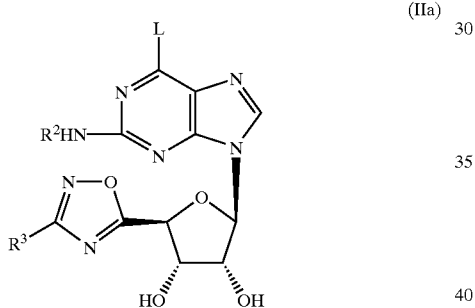
(IIa)

wherein L represents a leaving group eg. chlorine or a protected derivative thereof, with a compound of formula $R^1NH_2$, under conditions analogous to those described for the first process above.

Compounds of formula (IIa) may be prepared by reacting a compound of formula (XI)'

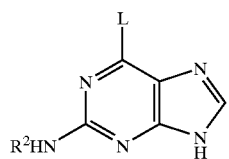
(XI)$^I$ (especially where L represents halogen eg. chlorine) with a compound of formula (X) under conditions analogous to those described for the third process.

Compounds of formula (XI)' may be prepared following Scheme 3 or by an analogous process.

We also provide a fifth process for the preparation of compounds of formula (I) in which $R^1$ represents hydrogen, which comprises conversion of a compound of formula (IIb)

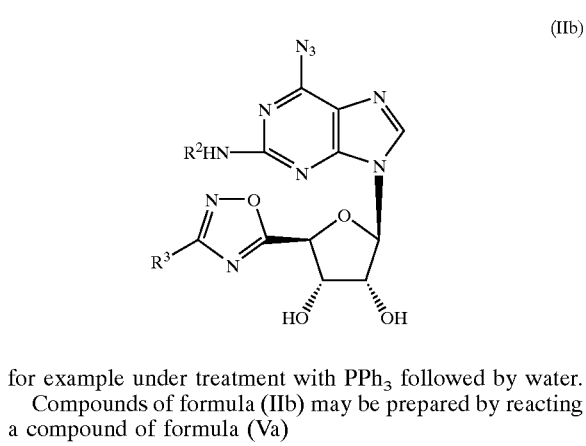
(IIb)

for example under treatment with $PPh_3$ followed by water.

Compounds of formula (IIb) may be prepared by reacting a compound of formula (Va)

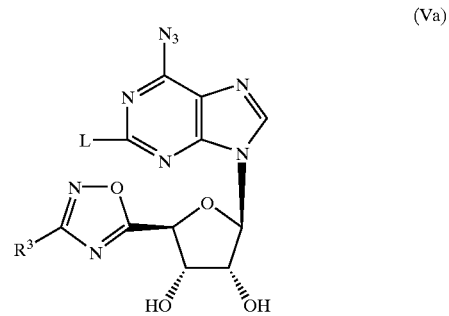
(Va)

with a compound of formula $R^2NH_2$ under conditions analogous to those described for the first process above.

Compounds of formula (Va) may be prepared by reacting a compound of formula (V) wherein $L^1$ and $L^2$ independently represent a leaving group especially halogen (e.g. chlorine) or a protective derivative thereof with a compound of formula $NaN_3$.

We further provide a sixth process for the preparation of compounds of formula (I) including the step of deprotecting a compound of formula (I) which is protected and where desired or necessary converting a compound of formula (I) or a salt thereof into another salt thereof Compounds of formula $R^1NH_2$, $R^2NH_2$ and $OH-N=C(R^3)NH_2$ are either known or may be prepared by known methods.

Examples of protecting groups where referred to in this patent application and the means for their removal can be found in T W Greene "Protective Groups in Organic Synthesis" (J Wiley and Sons, 1991). Suitable hydroxyl protecting groups include alkyl (e.g. methyl), acetal (e.g. acetonide) and acyl (e.g. acetyl or benzoyl) which may be removed by hydrolysis, and arylalkyl (e.g. benzyl) which may be removed by catalytic hydrogenolysis. Suitable amine protecting groups include sulphonyl (e.g. tosyl), acyl e.g. benzyloxycarbonyl or t-butoxycarbonyl) and arylalkyl (e.g. benzyl) which may be removed by hydrolysis or hydrogenolysis as appropriate.

Suitable salts of the compounds of formula (I) include physiologically acceptable salts such as acid addition salts derived from inorganic or organic acids, for example hydrochlorides, hydrobromides, sulphates, phosphates, acetates, benzoates, citrates, succinates, lactates, tartrates, fumarates, maleates, 1-hydroxy-2-naphthoates, methanesulphonates, and if appropriate, inorganic base salts such as alkali metal salts, for example sodium salts. Other salts of the compounds of formula (I) include salts which are not physiologically acceptable but may be useful in the preparation of compounds of formula (I) and physiologically acceptable salts thereof. Examples of such salts include trifluoroacetates and formates.

Examples of suitable solvates of the compounds of formula (I) include hydrates.

Acid-addition salts of compounds of formula (I) may be obtained by treating a free-base of formula (I) with an appropriate acid.

The potential for compounds of formula (I) to inhibit leukocyte function may be demonstrated, for example, by their ability to inhibit superoxide ($O_2^-$) generation from neutrophils stimulated with chemoattractants such as N-formylmethionyl-leucyl-phenylalanine (fMLP). Accordingly, compounds of formula (I) are of potential therapeutic benefit in providing protection from leukocyte-induced tissue damage in diseases where leukocytes are implicated at the site of inflammation.

Examples of disease states in which the compounds of the invention have potentially beneficial anti-inflammatory effects include diseases of the respiratory tract such as adult respiratory distress syndrome (ARDS), bronchitis (including chronic bronchitis), cystic fibrosis, asthma (including allergen-induced asthmatic reactions), emphysema, rhinitis and septic shock. Other relevant disease states include diseases of the gastrointestinal tract such as intestinal inflammatory diseases including inflammatory bowel disease (e.g. Crohn's disease or ulcerative colitis), *Helicobacter-pylori* induced gastritis and intestinal inflammatory diseases secondary to radiation exposure or allergen exposure, and non-steroidal anti-inflammatory drug-induced gastropathy. Furthermore, compounds of the invention may be used to treat skin diseases such as psoriasis, allergic dermatitis and hypersensitivity reactions and diseases of the central nervous system which have an inflammatory component eg Alzheimer's disease and multiple sclerosis.

Further examples of disease states in which compounds of the invention have potentially beneficial effects include cardiac conditions such as peripheral vascular disease, post-ischaemic reperfusion injury and idiopathic hypereosinophilic syndrome.

Compounds of the invention which inhibit lymphocyte function may be useful as immunosuppressive agents and so have use in the treatment of auto-immune diseases such as rheumatoid arthritis and diabetes.

Compounds of the invention may also be useful in inhibiting metastasis or in promoting wound healing.

It will be appreciated by those skilled in the art that reference herein to treatment extends to prophylaxis as well as the treatment of established conditions.

As mentioned above, compounds of formula (I) are useful in human or veterinary medicine, in particular as anti-inflammatory agents.

There is thus provided as a further aspect of the invention a compound of formula (I) or a physiologically acceptable salt or solvate thereof for use in human or veterinary medicine, particularly in the treatment of patients with inflammatory conditions who are susceptible to leukocyte-induced tissue damage.

According to another aspect of the invention, there is provided the use of a compound of formula (I) or a physiologically acceptable salt or solvate thereof for the manufacture of a medicament for the treatment of patients with inflammatory conditions who are susceptible to leukocyte-induced tissue damage.

In a further or alternative aspect there is provided a method for the treatment of a human or animal subject with an inflammatory condition who is susceptible to leukocyte-induced tissue damage, which method comprises administering to said human or animal subject an effective amount of a compound of formula (I) or a physiologically acceptable salt or solvate thereof.

The compounds according to the invention may be formulated for administration in any convenient way, and the invention therefore also includes within its scope pharmaceutical compositions for use in anti-inflammatory therapy, comprising a compound of formula (I) or a physiologically acceptable salt or solvate thereof together, if desirable, with one or more physiologically acceptable carriers or excipients.

There is also provided a process for preparing such a pharmaceutical formulation which comprises mixing the ingredients.

The compounds according to the invention may, for example, be formulated for oral, buccal, parenteral, topical or rectal administration, preferably for parenteral or topical (e.g. by aerosol) administration.

Tablets and capsules for oral administration may contain conventional excipients such as binding agents, for example syrup, acacia, gelatin, sorbitol, tragacanth, mucilage of starch, cellulose or polyvinyl pyrrolidone; fillers, for example, lactose, microcrystalline cellulose, sugar, maize-starch, calcium phosphate or sorbitol; lubricants, for example, magnesium stearate, stearic acid, talc, polyethylene glycol or silica; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxymethyl cellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The preparations may also contain buffer salts, flavouring, colouring and/or sweetening agents (e.g. mannitol) as appropriate.

For buccal administration the compositions may take the form of tablets or lozenges formulated in conventional manner.

The compounds may also be formulated as suppositories, e.g. containing conventional suppository bases such as cocoa butter or other glycerides.

The compounds according to the invention may also be formulated for parenteral administration by bolus injection or continuous infusion and may be presented in unit dose form, for instance as ampoules, vials, small volume infusions or pre-filled syringes, or in multi-dose containers with an added preservative. The compositions may take such forms as solutions, suspensions, or emulsions in aqueous or non-aqueous vehicles, and may contain formulatory agents such as anti-oxidants, buffers, antimicrobial agents and/or tonicity adjusting agents. Alternatively, the active ingredient may be in powder form for constitution with a suitable vehicle, e.g. sterile, pyrogen-free water, before use. The dry solid presentation may be prepared by filling a sterile powder aseptically into individual sterile containers or by filling a sterile solution aseptically into each container and freeze-drying.

By topical administration as used herein, we include administration by insufflation and inhalation. Examples of various types of preparation for topical administration include ointments, creams, lotions, powders, pessaries, sprays, aerosols, capsules or cartridges for use in an inhaler or insufflator, solutions for nebulisation or drops (e.g. eye or nose drops).

Ointments and creams may, for example, be formulated with an aqueous or oily base with the addition of suitable thickening and/or gelling agents and/or solvents. Such bases may thus, for example, include water and/or an oil such as liquid paraffin or a vegetable oil such as arachis oil or castor oil or a solvent such as a polyethylene glycol. Thickening agents which may be used include soft paraffin, aluminium stearate, cetostearyl alcohol, polyethylene glycols, microcrystalline wax and beeswax.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents or suspending agents.

Spray compositions may be formulated, for example, as aqueous solutions or suspensions or as aerosols delivered from pressurised packs, with the use of a suitable propellant, e.g. dichlorodifluoromethane, trichlorofluoromethane, dichlorotetra-fluoroethane, 1,1,1,2,3,3,3-heptafluoropropane, 1,1,1,2-tetrafluoroethane, carbon dioxide or other suitable gas.

Intranasal sprays may be formulated with aqueous or non-aqueous vehicles with the addition of agents such as thickening agents, buffer salts or acid or alkali to adjust the pH, isotonicity adjusting agents or anti-oxidants.

Capsules and cartridges of for example gelatin, or blisters of for example laminated aluminium foil, for use in an inhaler or insufflator may be formulated containing a powder mix of a compound of the invention and a suitable powder base such as lactose or starch.

Solutions for inhalation by nebulation may be formulated with an aqueous vehicle with the addition of agents such as acid or alkali, buffer salts, isotonicity adjusting agents or antimicrobials. They may be sterilised by filtration or heating in an autoclave, or presented as a non-sterile product.

The pharmaceutical compositions according to the invention may also be used in combination with other therapeutic agents, for example anti-inflammatory agents (such as corticosteroids (eg fluticasone propionate, beclomethasone dipropionate, mometasone furoate, triamcinolone acetonide or budesonide) or NSAIDs (eg sodium cromoglycate)) or beta adrenergic agents (such as salmeterol, salbutamol, formoterol, fenoterol or terbutaline and salts thereof) or antiinfective agents (eg antibiotics, antivirals).

The invention thus provides, in a further aspect, a combination comprising a compound of formula (I) or a physiologically acceptable salt or solvate thereof together with another therapeutically active agent, for example an anti-inflammatory agent such as a corticosteroid or NSAID.

The combination referred to above may conveniently be presented for use in the form of a pharmaceutical formulation and thus pharmaceutical formulations comprising a combination as defined above together with a pharmaceutically acceptable carrier thereof represent a further aspect of the invention.

The individual components of such combinations may be administered either sequentially or simultaneously in separate or combined pharmaceutical formulations. Appropriate doses of known therapeutic agents will be readily appreciated by those skilled in the art.

Compounds of the invention may conveniently be administered in amounts of, for example, 0.01 to 500 mg/kg body weight, preferably 0.01 to 100 mg/kg body weight, 1 to 4 times daily. The precise dose will of course depend on the age and condition of the patient and the particular route of administration chosen.

Certain intermediate compounds described herein are new and these are also provided as an aspect of the invention.

The compounds of the invention have the advantage that they may be more efficacious, show greater selectivity, have fewer side effects, have a longer duration of action, be more bioavailable by the preferred route, show less systemic activity when administered by inhalation or have other more desirable properties than similar known compounds.

In particular the compounds of the invention have the advantage that they may show greater selectivity for the adenosine 2a receptor subtype over other adenosine receptor subtypes (especially the A1 and A3 receptor subtypes) than hitherto known compounds.

Compounds of the invention may be tested for in vitro and in vivo biological activity in accordance with the following screens:

(1) Agonist activity against adenosine 2a, adenosine 1 and adenosine 3 receptor subtypes.

Agonist selectivity of compounds against other human adenosine receptors is determined using Chinese hamster ovary (CHO) cells transfected with the gene for the relevant human adenosine receptor following a method based on that of Castanon and Spevak, 1994. The CHO cells are also transfected with cyclic AMP response elements promoting the gene for secreted placental alkaline phosphatase (SPAP) (Wood, 1995). The effect of test compounds may be determined by their effects on basal levels of cAMP (A2a) or on forskolin-enhanced cAMP (A1 and A3) as reflected by changes in levels of SPAP. $EC_{50}$ values for compounds may then be determined as a ratio to that of the non-selective agonist N-ethyl carboxamide adenosine (NECA).

(2) Antigen-induced lung eosinophil accumulation in sensitised guinea pigs.

Ovalbumin sensitised guinea pigs are dosed with mepyramine (1 mg/kg ip) to protect against anaphylactic bronchospasm. A compound of the invention is then given by the inhaled route (30 min breathing of an aerosol of the compound) immediately prior to ovalbumin challenge (30 min breathing of an aerosol generated from a 50 ug/ml solution of ovalbumin). Twenty four hours after challenge, the guinea pigs are killed and the lungs lavaged. Total and differential leukocyte counts are then obtained for the bronchoalveolar lavage fluid and the dose of test compound giving a 50% reduction in eosinophil accumulation ($ED_{50}$) is determined (Sanjar et al. 1992).

References:
Asako H, Wolf, R E, Granger, D N (1993), Gastroenterology 104, pp 31–37;
Bedford C D, Howd R A, Dailey O D, Miller A, Nolen H W III, Kenley R A, Kern J R, Winterle J S, (1986), J. Med. Chem. 29, pp2174–2183;
Burkey T H, Webster, R O, (1993), Biochem. Biophys Acta 1175, pp 312–318;
Castanon M J, Spevak W, (1994), Biochem. Biophys Res. Commun. 198, pp 626–631;
Cronstein B N, Kramer S B, Weissmann G, Hirschhorn R, (1983), Trans. Assoc. Am. Physicians 96, pp 384–91;
Cronstein B N, Kramer S B, Rosenstein E D, Weissmann G, Hirschhorn R, (1985), Ann N.Y. Acad. Sci. 451, pp 291–301;
Cronstein B N, Naime D, Ostad E, (1993), J. Clin. Invest. 92, pp 2675–82;
Cronstein B N, Naime D, Ostad E, (1994), Adv. Exp. Med. Biol., 370, pp 411–6;
Cronstein B N, (1994), J. Appl. Physiol. 76, pp 5–13;
Dianzani C, Brunelleschi S, Viano I, Fantozzi R, (1994), Eur. J. Pharmacol 263, pp 223–226;
Elliot K R F, Leonard E J, (1989), FEBS Letters 254, pp 94–98;
Flora K P, van't Riet B, Wampler G L, (1978), Cancer Research, 38, pp1291–1295;
Green P G, Basbaum A I, Helms C, Levine J D, (1991), Proc. Natl. Acad Sci. 88, pp 4162–4165;
Hirschorn R, (1993), Pediatr. Res 33, pp S35–41;
Kohno Y; Xiao-duo J; Mawhorter S D; Koshiba M; Jacobson K A. (1996).Blood 88 p3569–3574.
Peachell P T, Lichtenstein L M, Schleimer R P, (1989), Biochem Pharmacol 38, pp 1717–1725;
Richter J, (1992), J. Leukocyte Biol. 51, pp 270–275;
Rosengren S, Bong G W, Firestein G S, (1995), J. Immunol. 154, pp 5444–5451;
Sanjar S, McCabe P J, Fattah D, Humbles A A, Pole S M, (1992), Am. Rev. Respir. Dis. 145, A40;
Skubitz K M, Wickman N W, Hammerschmidt D E, (1988), Blood 72, pp 29–33
Van Schaick E A; Jacobson K A; Kim H O; Ijzerman A P; Danhof M. (1996) Eur J Pharmacol 308 p311–314.
Wood K V. (1995) Curr Opinion Biotechnology 6 p50–58.
The invention is illustrated by the following Examples:

EXAMPLES

General experimental details

Where products were purified by column chromatography, 'flash silica' refers to silica gel for chromatography, 0.040 to 0.063 mm mesh (e.g. Merck Art 9385), where column elution was accelerated by an applied pressure of nitrogen at up to 5 p.s.i. 'Biotage' refers to the use of the Biotage Flash 40 system using pre-packed normal phase silica columns where solvent elution was accelerated by an applied pressure of nitrogen upto 20 p.s.i.. Where thin layer chromatography (TLC) has been used it refers to silica gel TLC using 5×10 cm silica gel 60 $F_{254}$ plates (e.g. Merck Art 5719), visualised by UV light unless otherwise indicated.

Where products were purified by preparative HPLC, this was carried out on a C18-reverse-phase column (1% Dynamax™, eluting with a gradient of acetonitrile (containing 0.1% trifluoroacetic acid) in water (containing 0.1% trifluoroacetic acid) and the compounds isolated as their trifluoroacetate salts unless otherwise specified.

Standard Automated Preparative HPLC column, conditions & eluent

Automated preparative high performance liquid chromatography (autoprep. HPLC) was carried out using a Supelco™ ABZ+5 μm 100 mm×22 mm i.d. column eluted with a mixture of solvents consisting of i) 0.1% formic acid in water and ii) 0.05% formic acid in acetonitrile, the eluent being expressed as the percentage of ii) in the solvent mixture, at a flow rate of 4 ml per minute. Unless otherwise stated the eluent was used as a gradient of 5–95% over 20 minutes.

LC/MS System

The Liquid Chromatography Mass Spectroscopy (LC/MS) systems used:

LCIMS System A—A Supelco™ ABZ+, 3.3 cm×4.6 mm i.d. column eluting with solvents: A—0.1% v/v formic acid+0.077% w/v ammonium acetate in water, and B—95:5 acetonitrile:water+0.05% v/v formic acid. The following gradient protocol was used: 100% A for 0.7 mins; A+B mixtures, gradient profile 0–100% B over 3.5 mins; hold at 100% B for 3.5 mins; return to 0% B over 0.3 mins. Positive and negative electrospray ionization was employed.

LC/MS System B—A Supelco™ ABZ+, 5 cm×2.1 mm i.d. column eluting with solvents: A—0.1% v/v formic acid+0.077% w/v ammonium acetate in water, and B—95:5 acetonitrile:water+0.05% v/v formic acid. The following gradient protocol was used: 0–100% B over 3.5 mins; hold at 100% B for 1.50 mins; return to 0% B over 0.50 mins. Positive and negative electrospray ionization was employed.

LC/MS System C—A Supelco™ ABZ+, 3.3 cm×4.6 mm i.d. column eluting with solvents: A—0.1% v/v formic acid+10 mmol ammonium acetate in water, and B—95:5 acetonitrile:water+0.05% v/v formic acid. The following gradient protocol was used: 100% A for 0.7 mins; A+B mixtures, gradient profile 0–100% B over 3.7 mins; hold at 100% B for 0.9 mins; return to 0% B over 0.2 mins. Positive and negative electrospray ionization was employed.

Intermediates

Intermediate 1: (6R-{6-(2,2-Diphenyl-ethylamino)-2-[2-(1-methyl-1H-imidazol-4-yl)-ethylamino]-purin-9-yl}-2,2-dimethyl-tetrahydro-(3aR,6aR)-furo[3,4-d][1,3]dioxol-4R-yl)-methanol.

2-Chloro-N-(2,2diphenylethyl)-2,3,O-(1-methylethylidene)-adenosine, [Preparation 3. from International Patent Application No. WO 94/17090], (0.20 g, 0.384 mmol) was added to 2-(1-methyl-1H-imidazol-4-yl) ethylamine (0.24 g, 1.92 mmol, generated from the corresponding bis-hydrochloride by neutralisation with a slight deficiency of solid sodium hydroxide in methanol), and the solvent was removed by evaporation. DMSO (0.7 ml) was added to the residue to form a slurry, which was heated at 90° C. for 25 h. The cooled reaction mixture was purified by column chromatography on flash silica (200:5:1–200:10:1, DCM:MeOH:NH$_3$) to give the title compound as a white solid (0.226 g). LC/MS SYSTEM A $R_t$=3.97 mins, m/z 611 MH$^+$ Intermediate 2: (3aS,4S,6R,6aR)-6-{6-(2,2-Diphenyl-ethylamino)-2-[2-(1-methyl-1H-imidazol-4-yl)-ethylamino]-purin-9-yl}-2,2-dimethyl-tetrahydro-furo[3,4-d][1,3]dioxole-4-carboxylic acid.

A solution of Intermediate 1 (0.226 g, 0.370 mmol) in 1,4 dioxan (3 ml), and water (1 ml) was added dropwise to a stirring purple solution of potassium permanganate (0.292 g, 1.85 mmol), and potassium hydroxide (0.166 g, 2.96 mmol) in water (1 ml) at 0° C. The resultant solution was stirred at 0° C. for 3 h, then treated with solid sodium metabisulphite until the purple colour was discharged. The resultant grey slurry was acidified to pH3, with hydrochloric acid solution (2N), and the product was extracted into ethylacetate (3×20 ml). The organics were washed with brine (20 ml), and dried ($MgSO_4$), then concentrated in vacuo to afford the title compound as a white solid (0.100 g). LC/MS SYSTEM A $R_t$=3.96 mins, m/z=625 $MH^+$ Intermediate 3: {2-Chloro-9-[6S-(3-ethyl-[1,2,4]oxadiazol-5-yl)-2,2-dimethyl-tetrahydro-(3aR,6aS)-furo[3,4-d][1,3] dioxol-4R-yl]-9H-purin-6-yl}-(2,2-diphenyl-ethyl)-amine.

Diisopropylethylamine (0.218 ml, 1.214 mmol) was added a stirring mixture of (3aS,4S,6R,6aR)-6-[2-chloro-6-(2,2-diphenyl-ethylamino)-purin-9-yl]-2,2-dimethyl-tetrahydro-furo[3,4-d][1,3]dioxole-4-carboxylic acid [Preparation 4. from International Patent Application No. WO 94/17090] (0.50 g, 0.935 mmol), in dry tetrahydrofuran (10 ml), at 0° C. Pivaloyl chloride (0.150 ml, 1.214 mmol) was added to the cooled stirring mixture, and it was stirred for at 0° C. for 1 h. The mixture was cooled to −10° C., and N-hydroxy-propionamidine, (0.160 g, 1.87 mmol) in dry tetrahydrofuran (3 ml) was added dropwise, and the resultant solution stirred for 1 h. The mixture was allowed to warm to room temperature and stirred for a further 20 h. The solution was concentrated in vacuo, then azeotroped with toluene (2×10 ml). The yellow residue was re-dissolved in toluene (15 ml), and heated at 80° C. with stirring for 1 h. Once cool the reaction mixture was concentrated in vacuo to give a yellow oil, which was purified by column chromatography on flash silica (35–50% ethylacetate-cyclohexane) to give the title compound as a white solid (0.430 g). TLC (35% ethylacetate-cyclohexane) rf=0.58

Intermediate 4: (2R,3R,4S,5S)-2-[2-Chloro-6-(2,2-diphenyl-ethylamino)-purin-9-yl]-5-(3-ethyl-[1,2,4] oxadiazol-5-yl)-tetrahydro-furan-3,4-diol.

A solution of Intermediate 3 (0.375 mg, 0.638 mmol) in a mixture of trifluoroacetic acid (5.6 ml) and water (1.4 ml), was stirred at 5–10° C. under nitrogen for 8.5 h, then concentrated in vacuo. The residue was azeotroped with toluene (2X), to produce the title compound as a cream coloured solid (0.340 mg). LC/MS system B $R_t$=3.36 mins, m/z=548 $MH^+$ Intermediate 5: 2-Chloro-N-(1-Ethylpropyl)-adenosine A mixture of 2,6-dichloro-9-(2,3,5-tri-O-acetyl-β-D-ribofuranosyl)-9H-purine ** (10.1 g, 22.6 mM), isopropanol (300 ml), $K_2CO_3$ (5 g) and 1-ethylpropylamine (2.17 g, 24.84 mM) was stirred at 20 C. for 24 hrs. The reaction mixture was heated at 54° C. for 73 hrs. Solvent was removed in vacuo, water (50 ml) was added, extracted with ethyl acetate (3×80 ml), the combined extracts were dried ($MgSO_4$) affording the title compound as a creamy light brown foam (9.44 g). LC/MS system A $R_t$=2.66 min, m/z= 372 $MH^+$.

** M. J. Robins and B. Uznanski, *Canad. J. Chem.*, 1981, 59(17), 2608

Intermediate 6: {6R-[2-Chloro-6-(1-ethyl-propylamino)-purin-9-yl]-2,2-dimethyl-tetrahydro-(3aR,6aR)-furo[3,4-d] [1,3]dioxol-4R-yl}-methanol A mixture of Intermediate 5 (9.3 g, 22.6 mmol), 2,2-dimethoxypropane (35 ml), acetone (250 ml) and paratoluenesulfonic acid (8.1 g) was stirred for 22 hrs. at 20° C. The solvent was removed in vacuo and the residue taken up in ethyl acetate (200 ml), washed with sodium bicarbonate (aqueous, saturated, 3×70 ml). The aqueous washings were back extracted with ethyl acetate (50 ml). The combined organic layers were dried ($MgSO_4$) and solvent was removed in vacuo. The residue was purified by column chromatography on flash silica (50%, 60% and then 70% ethyl acetate-cyclohexane) to afford the title compound as a white foam (5.67 g). TLC $SiO_2$ (50% ethyl acetate in cyclohexane) Rf=0.17

Intermediate 7: (3aS,4S,6R,6aR)-6-[2-Chloro-6-(1-ethyl-propylamino)-purin-9-yl]-2,2-dimethyl-tetrahydro-furo[3,4-d][1,3]dioxole-4-carboxylic acid A mixture of Intermediate 6 (5.431 g, 13.2 mmol), KBr (0.157 g, 1.32 mmol), TEMPO, (0.010 g, 0.07 mmol) in ethyl acetate (205 ml) and saturated aqueous $NaHCO_3$ (138 ml) was vigorously stirred for 20 mins. at 0° C. A mixture made up of sodium hypochlorite (13% active chloride, 7.3 ml) solid $NaHCO_3$ (0.420 g) and water (2 ml) was added dropwise over 5 mins. After 30 mins. more reagents (KBr, TEMPO, sodium hypochlorite, solid $NaHCO_3$ and water in the same quantities as above) were added. This addition was repeated after a further 30 mins had elapsed. One hour later the reaction mixture was poured into aqueous solution of $Na_2SO_3$ (28 g) in water (400 ml), diluted with ethyl acetate (100 ml). The mixture was vigorously shaken and the organic phase washed with water (100 ml). The combined aqueous layers were cooled to 0° C. and acidified to pH 3 with 2M hydrochloric acid, extracted with ethyl acetate (3×200 ml), dried ($MgSO_4$) and solvent was removed in vacuo leaving the title compound as a white foam (5.03 g). LC/MS system B $R_t$=3.25 min, m/z=426 $MH^+$.

Intermediate 8: {2-Chloro-9-[6S-(3-ethyl-[1,2,4]oxadiazol-5-yl)-2,2-dimethyl-tetrahydro-(3aR,6aS)-furo[3,4-d][1,3] dioxol-4R-yl]-9H-purin-6-yl}-(1-ethyl-propyl)-amine Intermediate 7 (0.7 g, 1.647 mmol), in anhydrous tetrahydrofuran (12 ml) at 0° C. was treated with diisopropylethylamine (0.372 ml, 2.14 mmol), and pivaloyl chloride (0.263 ml, 2.14 mmol). The resultant solution was stirred at 1.5 h at 0° C., then was cooled further to (−10° C.), and N-hydroxy-propionamidine (0.289 g, 3.29 mmol) was added in tetrahydrofuran (5 ml) over 15 mins. The solution was stirred at 0–5° C. for 1 h, then at room temperature for 20 h. The reaction mixture was concentrated in vacuo then azeotroped with toluene (2×20 ml). The residue was dissolved in toluene (15 ml), then heated at 80° C. for 1 h. Once cool the solution was concentrated in vacuo, then purified by column chromatography on flash silica (35% ethyl acetate-cyclohexane) to give the title compound as a clear oil (0.780 g). TLC $SiO_2$ (30% ethyl acetate in cyclohexane) Rf=0.26. LC/MS system B $R_t$=3.53 min, m/z=478 $MH^+$.

Intermediate 9: (2R,3R,4S,5S)-2-[2-Chloro-6-(1-ethyl-propylamino)-purin-9-yl]-5-(3-ethyl-[1,2,4]oxadiazol-5-yl)-tetrahydro-furan-3,4-diol Intermediate 8 (0.78 g, 1.63 mmol) in trifluoroacetic acid/water (10:1, 5 ml), was stirred at 0° C. for 4.5 h. The mixture was concentrated in vacuo, azeotroped with toluene (3×10 ml), to afford the title compound as a pink solid (0.705 g). LC/MS system B $R_t$=3.05 min, m/z=438 $MH^+$.

Intermediate 10: {2-Chloro-9-[2,2-dimethyl-6S-(3-methyl-[1,2,4]oxadiazol-5-yl)-tetrahydro-(3aR,6aS)-furo[3,4-d][1, 3]dioxol-4R-yl]-9H-purin-6-yl}-(1-ethyl-propyl)-amine Intermediate 7 (0.7 g, 1.647 mmol), in anhydrous tetrahydrofuran (12 ml) at 0° C. was treated with diisopropylethylamine (0.372 ml, 2.14 mmol), and pivaloyl chloride (0.263 ml, 2.14 mmol). The resultant solution was stirred at 1.5 h at 0° C., then was cooled further to (−10° C.), and N-hydroxy-acetamidine (0.244 g, 3.29 mmol) was added in tetrahydrofuran (5 ml) over 15 mins. The solution was stirred at 0–5° C. for 1 h, then at room temperature for 20 h. The reaction mixture was concentrated in vacuo then azeotroped with toluene (2×20 ml). The residue was dissolved in toluene (15 ml), then heated at 80° C. for 1 h. Once cool the solution was concentrated in vacuo, then purified by column chromatography on flash silica (35% ethyl acetate-cyclohexane) to give the title compound as a clear oil (0.762 g). TLC SiO$_2$ (30% ethyl acetate in cyclohexane) Rf=0.24. LC/MS system B R$_t$=3.41 min, m/z=464 MH$^+$.

Intermediate 11: (2R,3R,4S,5S)-2-[2-Chloro-6-(1-ethyl-propylamino)-purin-9-yl]-5-(3-methyl-[1,2,4]oxadiazol-5-yl)-tetrahydro-furan-3,4-diol Intermediate 10 (0.76 g, 1.64 mmol) in trifluoroacetic acid/water (10:1), (5 ml), was stirred at 0° C. for 4.5 h. The mixture was concentrated in vacuo, azeotroped with toluene (3×10 ml), to afford the title compound as a pale pink solid (0.692 g). LC/MS system B R$_t$=2.92 min, m/z=424 MH$^+$.

Intermediate 12: 2-Chloroadenosine

A stream of ammonia was bubbled through anhydrous methanol (25 ml) for 30 mins. at 0° C. The solution was added to a mixture of 2,6-dichloro-9-(2,3,5-tri-O-acetyl-β-D-ribofuranosyl)-9H-purine ** (2.000 g, 4.5 mmol) in dry methanol (5 ml) and allowed to warm to 20° C. over 24 h. More ammonia was bubbled through the solution after a further 6 h and subsequently after a further 20 h. Solvent was removed in vacuo and the residue was purified by column chromatography on flash silica (neat ethyl acetate) to afford the title compound as a white solid (1.152 g). TLC SiO$_2$ (neat ethylacetate) Rf=0.15

** M. J. Robins and B. Uznanski, *Canad. J. Chem.*, 1981, 59(17), 2608

Intermediate 13: [6R-(6-Amino-2-chloro-purin-9-yl)-2,2-dimethyl-tetrahydro-(3aR,6aR)-furo[3,4-d][1,3]dioxol-4R-yl]-methanol To a stirred solution of Intermediate 12 (0.700 g, 2.3 mmol) in acetone (70 ml) was added 2,2-dimethoxypropane (1.70 m, 13.8 mmol) and para-toluenesulfonic acid (0.438 g, 2.3 mmol) and the reaction mixture was stirred overnight at 20° C. The solvent was removed in vacuo and taken up in ethyl acetate (150 ml). The suspension was shaken with sodium bicarbonate (aqueous, saturated, 3×50 ml) and water. The aqueous washings were back extracted with ethyl acetate (50 ml). The combined organic layers were dried (MgSO$_4$) and solvent was removed in vacuo to afford the title compound as a white solid (0.651 g). TLC SiO$_2$ (neat ethyl acetate) Rf=0.33

Intermediate 14: (3aS,4S,6R,6aR)-6-(6-Amino-2-chloro-purin-9-yl)-2,2-dimethyl-tetrahydro-furo[3,4-d][1,3]dioxole-4-carboxylic acid A solution of Intermediate 13 (0.400 g, 1.2 mmol) in 1,4-dioxane (12 ml) and water (4 ml) was added dropwise over 20 mins to a stirred solution of KMnO$_4$ (0.924 g, 5.8 mmol) and potassium hydroxide (0.524 g, 9.4 mmol) in water (4 ml) at 0° C. The mixture was stirred at 0° C. for a further 3 h. Solid sodium metabisulphite was added to discharge the purple colour and then acidified to pH 3 with 2N HCl. The mixture was extracted with ethyl acetate (3×50 ml), the combined organic solutions were washed with brine, dried (MgSO$_4$), solvent was removed in vacuo to afford the title compound as a white solid (0.316 g). TLC SiO$_2$ (neat ethyl acetate) Rf=0.10

Intermediate 15: 2-Chloro-9-[2,2-dimethyl-6S-(3-methyl-[1,2,4]oxadiazol-5-yl)-tetrahydro-(3aR,6aS)-furo[3,4-d][1,3]dioxol-4R-yl]-9H-purin-6-ylamine Intermediate 14 (0.400 g), diisopropylethylamine (0.154 ml) in tetrahydrofuran (10 ml) were stirred for 15 min under nitrogen at room temperature then cooled to 0° C. Pivaloylchloride (0.18 ml) was added and the mixture stirred at 0° C. for 1 hr. The mixture was treated with N-hydroxy-acetamidine (0.196 g), stirred at 0° C. for 1 hr, then allowed to warm up to room temperature overnight. The reaction mixture was concentrated in vacuo, toluene (20 ml) added and the mixture heated at 80° C. for 3 hrs. The cooled mixture was evaporated in vacuo. Purification by column chromatography on flash silica eluted with [dichloromethane:ethanol:880 ammonia (100:8:1)] furnished the title compound as a white solid (0.328 g). TLC SiO$_2$ (Dichloromethane:ethanol:880 NH$_3$ 100:8:1) Rf=0.47

Intermediate 16: 2-Chloro-9-[6S-(3-ethyl-[1,2,4]oxadiazol-5-yl)-2,2-dimethyl-tetrahydro-(3aR,6aS)-furo[3,4-d][1,3]dioxol-4R-yl]-9H-purin-6-ylamine Intermediate 14 (0.500 g), diisopropylethylamine (0.318 ml) in tetrahydrofuran (10 ml) were cooled to 0° C. and stirred for 15 min under nitrogen. Pivaloylchloride (0.225 ml) was added and the mixture stirred for 1 hr at 0° C. The mixture was treated with N-hydroxy-propionamidine (0.246 g) in tetrahydrofuran (2 ml), stirred for 1 hr at 0° C., then allowed to warm up to room temperature overnight. The cooled reaction mixture was evaporated in vacuo. Purification by column chromatography on flash silica eluted with dichloromethane:ethanol:880 ammonia (100:8:1) to afford the title compound as a pale yellow foam (0.389 g) TLC SiO$_2$ (Dichloromethane:ethanol:880 NH$_3$ 100:8:1) Rf=0.5

Intermediate 17: (2R,3R,4S,5S)-2-(6-Amino-2-chloro-purin-9-yl)-5-(3-methyl-[1,2,4]oxadiazol-5-yl)-tetrahydro-furan-3,4-diol acetate Intermediate 15 (0.488 g) in acetic acid (20 ml) and water (5 ml) was heated at 100° C. for 16 hrs. The cooled reaction mixture was evaporated in vacuo to afford the title compound as a brown oil (0.537 g)

TLC SiO$_2$ (Dichloromethane:ethanol:880 NH$_3$ 100:8:1) Rf=0.14

Intermediate 18: (2R,3R,4S,5S)-2-(6-Amino-2-chloro-purin-9-yl)-5-(3-ethyl-[1,2,4]oxadiazol-5-yl)-tetrahydro-furan-3,4-diol acetate Intermediate 16 (0.381 g) in acetic acid (15 ml) and water(3 ml) was heated at 100° C. for 4.5 hrs, then at 119° C. for 3 hrs. More acetic acid (5 ml) and water (1 ml) was added and the reaction mixture heated at 119° C. for 8 hrs. The cooled reaction mixture was evaporated in vacuo to furnish the title compound as a light brown solid (0.410 g). TLC SiO$_2$ (Dichloromethane:ethanol:880 NH$_3$ 100:8:1) Rf=0.15.

Intermediate 19: [6R-(6-Amino-2-phenylethylamino-purin-9-yl)-2,2-dimethyl-tetrahydro-(3aR,6aS)-furo[3,4-d][1,3]dioxol-4R-yl]-methanol A solution of Intermediate 13 (10.0 g, 19.5 mmol) and phenylethylamine (12.2 ml, 97.3 mmol) was heated to 110° C. for 7 hrs. The reaction mixture was diluted with ethyl acetate (400 ml), washed with 1M HCl. The aqueous layer was re-extracted with ethyl acetate (3×200 ml) and the combined organic extracts were dried (MgSO$_4$), solvent was removed in vacuo and purified by column chromatography on flash silica eluted with 5% methanol in dichloromethane to afford the title compound as a brown oil (7.61 g) TLC SiO$_2$ (Dichloromethane:methanol, 10:1) Rf=0.28

Intermediate 20: (3aS,4S,6R,6aR)-(6-Amino-2-phenylethylamino-purin-9-yl)-2,2-dimethyl-tetrahydro-furo[3,4-d][1,3]dioxole-4-carboxylic acid A solution of Intermediate 19 (4.0 g, 9.38 mmol) in 1,4-dioxane (54 ml) and water (13.3 ml) was added dropwise over 30 mins. to a stirred solution of KMnO$_4$ (7.5 g, 46.9 mmol) and potassium hydroxide (4.24 g, 75 mmol) in water (84 ml) at 0° C. The mixture was stirred at 0° C. for a further 1 h. Excess KMnO$_4$ was destroyed by the portionwise addition of solid sodium metabisulphite, the solution was filtered through a pad of Celite and washed with further 1,4-dioxan. The filtrate was concentrated in vacuo to a volume of 20 ml, acidified with concentrated HCl. The solid formed was filtered and dried overnight over $P_2O_5$ to afford the title compound as a white solid (2.25 g). TLC $SiO_2$ (Dichloromethane:methanol, 5:1) Rf=0.44

Intermediate 21: 2-Phenylethylamino-9-[6S-(3-ethyl-[1,2,4] oxadiazol-5-yl)-2,2-dimethyl-tetrahydro-(3aR,6aS)-furo[3,4-d][1,3]dioxol-4R-yl]-9H-purin-6-ylamine To Intermediate 20 (0.500 g, 1.14 mmol) in DME (10 ml) was added N-hydroxy-acetamidine (0.168 g, 2.28 mmol) and EEDQ (0.654 g, 2.28 mmol) and was heated to reflux for 2 hrs. Further N-hydroxy-acetamidine (0.168 g, 2.28 mmol) and EEDQ (0.654 g, 2.28 mmol) were added and the reaction was heated at reflux for 4 days, the solvent was removed in vacuo and the residue was purified by column chromatography on flash silica eluted with 5% methanol in ethyl acetate to afford the title compound as a yellow foam (0.256 g). TLC $SiO_2$ (Ethyl acetate:methanol, 19:1) Rf=0.33

Intermediate 22: {2-Chloro-9-[2,2-dimethyl-6R-(3-propyl-[1,2,4]oxadiazol-5-yl)-tetrahydro-(3aS,6aR)-furo[3,4-d][1,3]dioxol-4S-yl]-9H-purin-6-yl}-(2,2-diphenyl-ethyl)-amine Diisopropylethylamine (0.181 ml, 1.04 mmol) was added to a stirring mixture of (3aS,4S,6R,6aR)-6-[2-chloro-6-(2,2-diphenyl-ethylamino)-purin-9-yl]-2,2-dimethyl-tetrahydro-furo[3,4-d][1,3]dioxole-4-carboxylic acid [Preparation 4, International Patent Application No. WO94/17090] (0.428 g, 0.8 mmol), in dry tetrahydrofuran (8 ml), at 0° C. Pivaloyl chloride (0.128 ml, 1.04 mmol) was added to the cooled mixture, and it was stirred at 0° C. for 1 h. N-Hydroxy-butyramidine, (0.163 g, 1.6 mmol) in dry tetrahydrofuran (7 ml) was added dropwise, over ten minutes, and the resultant solution stirred for 1 h at 0° C. The mixture was allowed to warm to room temperature and stirred for a further 20 h. The solution was concentrated in vacuo, then azeotroped with toluene (2×10 ml). The yellow residue was re-dissolved in toluene (15 ml), and heated at 80° C. with stirring for 1 h. Once cool the reaction mixture was concentrated in vacuo then purified by column chromatography on flash silica (40% ethylacetate-cyclohexane) to give the title compound as a clear oil (0.392 g). LC/MS system A $R_t$=5.27 mins, m/z=602 MH$^+$ Intermediate 23: (2R,3R,4S,5S)-2-[2-Chloro-6-(2,2-diphenyl-ethylamino)-purin-9-yl]-5-(3-propyl-[1,2,4] oxadiazol-5-yl)-tetrahydro-furan-3,4-diol A solution of Intermediate 22 (0.392 g, 0.652 mmol) in a mixture of acetic acid (10 ml) and water (2.5 ml), was stirred at 100° C. under nitrogen for 26 h, then concentrated in vacuo. The residue was azeotroped with toluene (2×10 ml), to produce the title compound as a beige foam (0.355 g). LC/MS system B $R_t$=3.41 mins, m/z=562 MH$^+$ Intermediate 24: {2-Chloro-9-[2,2-dimethyl-6S-(3-methyl-[1,2,4]oxadiazol-5-yl)-tetrahydro-(3aR,6aS)-furo[3,4-d][1,3]dioxol-4R-yl]-9H-purin-6-yl}-(2,2-diphenyl-ethyl)-amine Diisopropylethylamine (0.063 ml, 0.364 mmol) was added to a stirring mixture of (3aS,4S,6R,6aR)-6-[2-chloro-6-(2,2-diphenyl-ethylamino)-purin-9-yl]-2,2-dimethyl-tetrahydro-furo[3,4-d][1,3]dioxole-4-carboxylic acid [Preparation 4 in International Patent Application No. WO94/17090] (0.15 g, 0.28 mmol), in dry tetrahydrofuran (4 ml), at 0° C. Pivaloyl chloride (0.045 ml, 0.364 mmol) was added to the cooled stirring mixture, and it was stirred at 0° C. for 1.5 h. N-Hydroxy-acetamidine, (0.042 g, 0.56 mmol) was added portion-wise over 10 mins, and the resultant solution stirred for 1 h at 0° C. The mixture was allowed to warm to room temperature and stirred for a further 20 h. The solution was concentrated in vacuo, then azeotroped with toluene (2×10 ml). The yellow residue was re-dissolved in toluene (7 ml), and heated at 80° C. with stirring for 1 h. Once cool the reaction mixture was concentrated in vacuo to give the title compound as a yellow oil (0.146 g). LC/MS system B $R_t$=3.58 mins, m/z=574 MH$^+$ Intermediate 25: (2R,3R,4S,5S)-2-[2-Chloro-6-(2,2-diphenyl-ethylamino)-purin-9-yl]-5-(3-methyl-[1,2,4] oxadiazol-5-yl)-tetrahydro-furan-3,4-diol A solution of Intermediate 24 (0.146 g, 0.255 mmol) in a mixture of acetic acid (10 ml) and water (2.5 ml), was stirred at 100° C. under nitrogen for 37 h, then concentrated in vacuo. The residue was azeotroped with toluene (2×10 ml), to produce the title compound as a yellow solid (0.132 g). LC/MS system B $R_t$=3.23 mins, m/z=534 MH$^+$ Intermediate 26: {2-Chloro-9-[6S-(3-cyclopropyl-[1,2,4] oxadiazol-5-yl)-2,2-dimethyl-tetrahydro-(3aR,6aS)-furo[3,4-d][1,3]dioxol-4R-yl]-9H-purin-6-yl}-(1-ethyl-propyl)-amine Intermediate 7 (2.13 g, 5 mmol) dissolved in tetrahydrofuran(33 ml) under nitrogen was cooled to 5° C., N,N-diisopropylethylamine (1.9 ml, 11 mmol) and trimethylacetyl chloride (0.67 ml, 5.5 mmol) were added and mixture allowed to warm to room temperature over 1 h. After cooling to 5° C. N-Hydroxy-cyclopropanecarboxamidine** (0.61 g, 6 mmol) was added and the reaction mixture stirred for 16 h allowing warming to room temperature. Solvent was removed in vacuo and the residue was dissolved in toluene (100 ml) and heated to reflux (120° C.) under nitrogen for 24 h. Toluene was removed in vacuo and product purified by Solid Phase Extraction using Varian Mega Bonded Elut cartridge (10 g $SiO_2$) eluted with ethyl acetate/cyclohexane (1:2) to afford title compound as yellow gum (2.170 g). LCMS SYSTEM A $R_t$=4.80 mins m/z=490 MH$^+$

** W. J. Fanshawe, V. J. Bauer, S. R. Safir, D. A. Blickens and S. J.Riggi, J. Med. Chem., 1969, 12, 381

Intermediate 27: (2R,3R,4S,5S)-2-[2-Chloro-6-(1-ethyl-propylamino)-purin-9-yl]-5-(3-cyclopropyl-[1,2,4] oxadiazol-5-yl)-tetrahydro-furan-3,4-diol Intermediate 26 (2.1 g,4.5 mmol) was dissolved in trifluoroacetic acid/water (9:1, 25 ml) at 0° C. under nitrogen with stirring for 6 h. and left in refrigerator (4° C.) for 16 h. The mixture was concentrated in vacuo and poured slowly on to saturated sodium bicarbonate solution (150 ml), extracting with dichloromethane(3×50 ml), washing with brine, drying with sodium sulphate, filtering and concentrating to afford the title compound as a yellow-white solid (2 g). LCMS SYSTEM B $R_t$=3.22 mins m/z=450 MH$^+$ Intermediate 28: {6R-(2-Chloro-6-phenethylamino-purin-9-yl)-2,2-dimethyl-tetrahydro-(3aR,6aR)-furo[3,4-d][1,3]dioxol-4R-yl}methanol A mixture of acetic acid 4R-acetoxy-5R-acetoxymethyl-2R-(2,6-dichloro-purin-9-yl)-tetrahydro-furan-3R-yl ester** (0.1 g, 0.224 mmol), 2-phenylethylamine (0.034 ml, 0.27 mmol) and di-isopropylethylamine (0.047 ml, 0.27 mmol) in isopropanol (2 ml) was heated at 52° C. for 17.5 h in a sealed vial (e.g. Reactivial™). The reaction was then diluted with methanol (1 ml). A solution of sodium methoxide (25 wt % in methanol, 0.077 ml, 0.336 mmol) was added and stirred for 3.5 h at room temperature. Acetic acid (0.2 ml) was then added to the reaction mixture. Removal of volatile matters gave a residue which was dissolved in acetone (2.5 ml) and treated with 2,2-dimethoxypropane (0.35 ml) and paratoluenesulfonic acid (0.081 g). More reagents were added at 66 h [acetone (3 ml) and 2,2-dimethoxypropane (0.35 ml)] and 90 h [para-toluenesulfonic acid (81 mg)]. After a further 21 h reaction mixture was evaporated under a jet of air. The resultant mixture was stirred with saturated aqueous sodium carbonate (4 ml) for 10 mins., extracted with ethyl acetate (3×3 ml), dried ($MgSO_4$) and evaporated in vacuo to give the titled com pound as a light brown gum (0.118 g). LC/MS system A $R_t$=4.50 mins, m/z=446 MH$^+$ for $C_{21}H_{24}{}^{35}ClN_5O_4$.
** M. J. Robins and B. Uznanski, *Canad. J. Chem.*, 1981, 59(17), 2608

Intermediate 29: {6R-[2-Chloro-6-(2-cyclohexyl-ethylamino)-purin-9-yl]-2,2-dimethyl-tetrahydro-(3aR, 6aR)-furo[3,4-d][1,3]dioxol-4R-yl}-methanol Intermediate 29 was prepared in an analogous manner to Intermediate 28 using 2-cyclohexylethylamine (0.034 g, 0.27 mmol). The title compound was obtained as a light brown foam (0.116 g). LC/MS system A $R_t$=4.93 mins, m/z=452 MH$^+$ for $C_{21}H_{30}{}^{35}ClN_5O_4$.

Intermediate 30: {6R-[2-Chloro-6-(3,3-dimethyl-butylamino)-purin-9-yl]-2,2-dimethyl-tetrahydro-(3aR, 6aR)-furo[3,4-d][1,3]dioxol-4R-yl}-methanol Intermediate 30 was prepared in an analogous manner to Intermediate 28 using 3,3-dimethylbutylamine (0.036 ml, 0.27 mmol). The title compound was obtained as a white solid (0.111 g) in 88% purity. LC/MS system A $R_t$=4.93 mins, m/z=452 MH$^+$ for $C_{21}H_{30}{}^{35}ClN_5O_4$.

Intermediate 31: {6R-(6-phenethylamino)-2-[2-(1-methyl-1H-imidazol-4yl)-ethylamino]-purin-9-yl}-2,2-dimethyl-tetrahydro-(3aR,6aR)-furo[3,4-d][1,3]dioxol-4R-yl) methanol A mixture of Intermediate 28 (0.118 g, 0.265 mmol) and 2-(1-methyl-1H-imidazol-4-yl)ethylamine (0.168 g, 1.344 mmol) generated from the corresponding bis-hydrochloride by neutralisation with a slight deficiency of solid sodium hydroxide in methanol) in a mixture of di-isopropylethylamine (0.3 ml) and DMSO (0.3 ml) was heated in a sealed vial (e.g.-Reacti-vial™) for 20 h at 104° C. The cooled reaction mixture was diluted with aqueous sodium hydroxide (0.5M, 5 ml), extracted with dichloromethane (4×5 ml). Combined extracts were filtered through a Varian Mega Bond Elut cartridge (5 g Si, 20 ml size), eluted with dichloromethane, 50% EtOAc-cyclohexane, EtOAc and then 10% MeOH—EtOAc. Fractions containing the desired product were combined and evaporated in vacuo affording the titled product as a clear gum (0.107 g). TLC (10% MeOH—EtOAc, visualised by UV light) rf=0.13

Intermediate 32: {6R-{6-(2-cyclohexyl-ethylamino)-2-[2-(1-methyl-1H-imidazol-4-yl)-ethylamino]-purin-9-yl}-2,2-dimethyl-tetrahydro-(3aR,6aR)-furo[3,4-d][1,3]dioxol-4R-yl) methanol Intermediate 32 was prepared in an analogous manner to Intermediate 31 using Intermediate 29 (0.116 g, 0.257 mmol). The title compound was obtained as a clear gum (0.09 g). TLC (10% MeOH—EtOAc, visualised by UV light) rf=0.13

Intermediate 33: {6R-{6-(3,3-dimethyl-butylamino)-2-[2-(1-methyl-1H-imidazol-4-yl)-ethylamino]-purin-9-yl}-2,2-dimethyl-tetrahydro-(3aR,6aR)-furo[3,4-d][1,3]dioxol-4R-yl) methanol Intermediate 33 was prepared in an analogous manner to Intermediate 31 using Intermediate 30 (0.111 g, 0.261 mmol). The title compound was obtained as a clear gum (0.097 g). TLC (10% MeOH—EtOAc, visualised by UV light) rf=0.13

Intermediate 34: (3aS,4S,6R,6aR)-6-{6-phenethylamino-2-[2-(1-methyl-1H-imidazol-4-yl)-ethylamino]-purin-9-yl}-2,2-dimethyl-tetrahydro-furo[3,4-d][1,3]dioxole-4-carboxylic acid To a stirring mixture of potassium hydroxide (0.1 g) and potassium permanganate (0.158 g, 1 mmol) in water (1 ml) at 0° C., a solution of Intermediate 31 (0.107 g, 0.2 mmol) in dioxan (1.6 ml) was added dropwise over 5 mins. Mixture was stirred in ice-water bath for 4 h. Solid sodium metabisulphate was added until all purple coloration disappeared. Mixture was filtered through a short and compressed pad of Harbourlite. The resultant aqueous solution was carefully acidified to pH3–4 with 2M aqueous hydrochloric acid and washed with EtOAc (3×5 ml). The resultant aqueous solution was freeze-dried to give a white solid which was extracted with methanol (3 ml then 2×1 ml) to give the titled product as a creamy white solid (0.084 g). LC/MS system C $R_t$=2.43 mins, m/z=549 MH$^+$ Intermediate 35: (3aS ,4S ,6R,6aR)-6-{6-(2-cyclohexyl-ethylamino)-2-[2-1-methyl-1H-imidazol-4-yl)-ethylamino]-purin-9-yl}-2,2-dimethyl-tetrahydro-furo[3,4-d][1,3]dioxole-4-carboxylic acid Intermediate 35 was prepared in an analogous manner to Intermediate 34 using Intermediate 32 (0.09 g, 0.17 mmol). The title compound was obtained as a creamy white solid (0.081 g). LC/MS system C $R_t$=2.61 mins, m/z=555 MH$^+$ Intermediate 36: (3aS,4S,6R,6aR)-6-{6-(3,3-Dimethyl-butylamino)-2-[2-(1-methyl-1H-imidazol-4-yl)-ethylamino]-purin-9-yl}-2,2-dimethyl-tetrahydro-furo[3,4-d][1,3]dioxole-4-carboxylic acid Potassium hydroxide (0.09 g, 1.52 mmol) was crushed and dissolved in water (0.5 ml) with stirring. Potassium permanganate (0.158 g, 0.95 mmol) was added with stirring and the mixture cooled to 0° C. to this was added Intermediate 33 (0.097 g, 0.19 mmol) dissolved in 1,4-dioxane (1.6 ml) and water (0.5 ml), pre-cooled to 0° C. The reaction mixture was stirred for 3 h at 0° C. then treated with solid sodium metabisulphite (0.15 g) until the purple colour discharged. Insolubles were filtered off through a pad of Harborlite washing with water (10 ml). The aqueous mixture was extracted with dichloromethane (2×20 ml). Combined organics were concentrated in vacuo to afford title compound as a yellow oil (0.064 g). LCMS SYSTEM C Rt=2.44 min m/z=529 MH$^+$ Intermediate 37: 2-(Pyridin-2-ylamino)-ethylamine 2-Bromopyridine (10.00 g, 63.3 mmol) was added dropwise to 1,2-diaminoethane (76.00 g, 126.6 mmol) under nitrogen at 20° C. with stirring. The reaction mixture was stirred at 20° C. for 4 h. and then under reflux for 24 h. The reaction mixture was concentrated in vacuo and purified by column chromatography on flash silica eluting with dichloromethane, ethanol and ammonia (30:8:1) to afford the title compound as a red oil (1.23 g). TLC $SiO_2$, (Dichloromethane, ethanol, ammonia; 30:8:1) Rf=0.14 Mass Spectrum m/z 138 (MH$^+$ for $C_7H_{11}N_3$).

Intermediate 38: N-Hydroxy-propionamidine

A mixture of propionitrile (20 ml, 280 mmol), potassium carbonate (78 g, 560 mmol) and hydroxylamine hydrochloride (19.000 g, 280 mmol) in ethanol (400 ml) was stirred at room temperature for 15 min and slowly heated to reflux over 1 hour and refluxed for 7 hours. On cooling the mixture was filtered through Harbolite filter aid, washed with ethanol (100 ml). The solvent was evaporated in vacuo and the residue was azeotroped with toluene (3×100 ml) to afford the title compound as a light coloured oil (17 g) TLC $SiO_2$ (5% methanol/chlorofrom/1% ammonia) Rf=0.21

Intermediate 39: 3-Ethyl-5-(6R-methoxy-2,2-dimethyl-tetrahydro-(3aR,6aR)-furo[3,4-d][1,3]dioxol-4S-yl)-[1,2,4]oxadiazole A mixture of (3aS,4S,6R,6aR)-Methoxy-2,2-dimethyl-tetrahydro-furo[3,4-d][1,3]dioxole-4-carboxylic acid, prepared by following the method of Intermediate 1 in International Patent Application No. WO098/28319, (14.800 g, 68 mmol), 1-hydroxybenzatriazole (9.200 g, 68 mmol), and 1(3-dimethylaminopropyl)-3-ethyl carbodiimide hydrochloride (13.000 g, 68 mmol) in DMF (200 ml) was stirred at room temperature overnight. Intermediate 38 (6.000 g, 68 mmol) in DMF (10 ml) was then added and the mixture heated to 70° C. overnight. Upon cooling the solvent was removed in vacuo. The residue was taken up into ethyl acetate (100 ml) and washed with 10% citric acid (2×100 ml), water (1×100 ml) and the organic layer was dried (MgSO$_4$) and evaporated in vacuo to afford the title compound as a colourless gum (17.00 g). LC/MS SYSTEM C R$_t$=1.77 mins, m/z=271 MH$^+$ Intermediate 40: Acetic acid 4S-acetoxy-2R-(3-ethyl-[1,2,4] oxadiazol-5-yl)-5S-methoxy-tetrahydro-furan-3R-yl ester A mixture of Intermediate 39 (17 g, 62 mmol) and concentrated hydrochloric acid (3 ml) in methanol (200 ml) was heated to reflux overnight. On cooling the mixture was evaporated in vacuo to 50% volume, and pyridine (50 ml) was added. The mixture was then evaporated in vacuo to approximately 25% of original volume. Additional pyridine (100 ml) was added and the mixture was evaporated in vacuo. The residue was taken up into anhydrous pyridine (150 ml) and treated with acetic anhydride (50 ml, excess) followed DMAP (0.38 g 3 mmol). The mixture was stirred at room temperature overnight. The mixture was evaporated, the residue was taken up into ethyl acetate (200 ml) and washed with 10% citric acid (2×100 ml), water (100 ml), dried (MgSO$_4$) and the solvent was removed in vacuo. Purification using flash column chromatography with a Biotage column (3×90 g, SiO$_2$) eluted with 30% cyclohexane, ethyl acetate furnished the title compound as a colourless solid (17.500 g). TLC SiO$_2$ (50% cyclohexanel ethyl acetate) Rf=0.52

Intermediate 41: Acetic acid 4S-acetoxy-2R-(2,6-dichloro-purin-9-yl)-5S-(3-ethyl-[1,2,4]oxadiazol-5-yl)-tetrahydro-furan-3R-yl ester A mixture of 2,6-dichloropurine (0.829 g, 4.3 mmol) in 1,1,1,3,3,3,hexamethyldisilazane (5 ml) was heated to reflux overnight, then the solvent was removed in vacuo. The residue obtained was azeotroped with anhydrous toluene (3×5 ml). To the residue in anhydrous acetonitrile (2 ml) was added Intermediate 40 (0.500 g, 1.6 mmol) and DBU (0.65 ml, 4.3 mmol). The mixture was then cooled to 0° C. and the TMSOTf (0.9 ml, 4.8 mmol) was added. The mixture was allowed to warm to room temperature, and the heated to reflux overnight giving a deep red coloured solution. On cooling the mixture was poured into saturated bicarbonate solution (5 ml) and extracted with ethyl acetate (3×10 ml). The combined organic layers was washed with water (20 ml), dried (MgSO$_4$) and the solvent removed in vacuo. The residue obtained was purified using flash column chromatography with a Biotage column (8 g, SiO$_2$) eluting with 60% cyclohexane, ethyl acetate to afford the title compound as an off white solid (0.599 g). LC/MS SYSTEM C R$_t$=3.32 mins, m/z=472 MH$^+$ Intermediate 42: Acetic acid 4S-acetoxy-2R-[6-azido-2-(1S-hydroxymethyl-2-phenyl-ethylamino)-purin-9-yl]-5S-(3-ethyl-[1,2,4]oxadiazol-5yl)-tetra hydro-furan-3R-yl ester To a cooled mixture of Intermediate 41 (0.600 g, 1.27 mmol) in anhydrous DMF at −10 to −15° C. was added sodium azide (0.088 g, 1.35 mmol). The mixture was stirred at −10° C. for 2 hours and 3-(S)-(−)2-amino-3-phenyl propanol (0.388 g, 2.8 mmol) in anhydrous DMF (1 ml) was added. The mixture was allowed to warm to room temperature and stirred overnight. Water(15 ml) was added and the mixture was extracted with ethyl acetate (3×15 ml). The combined organic phases were dried (MgSO$_4$) and evaporated in vacuo. Purification using flash column chromatography with a Biotage column (8 g, SiO$_2$) eluting with 30% cyclohexane, ethyl acetate, furnished the title compound as a colourless gum (0.450 g). LC/MS SYSTEM C R$_t$=3.25 min, m/z=593 MH$^+$ Intermediate 43: Acetic acid 4S-acetoxy-2R-[6-amino-2-(1S-hydroxy methyl-2-phenyl-ethylamino)-purin-9-yl]-5S-(3-ethyl-[1,2,4]oxadiazol-5-yl)-tetrahydro-furan-3R-yl ester A mixture of Intermediate 42 (0.440 g, 0.74 mmol) and triphenylphosphine (0.220 g, 0.84 mmol) in tetrahydrofuran (5 ml) was stirred at room temperature overnight. The solvent was evaporated in vacuo. Purification using Autoprep. HPLC afforded the title compound as an off-white solid (0.410 g). LC/MS SYSTEM C R$_t$=2.77 min, m/z=567 MH$^+$

EXAMPLES

Example 1

(2R,3R,4S,5S)-2-{6-(2,2-Diphenyl-ethylamino)-2-[2-(1-methyl-1H-imidazol-4-yl)-ethylamino]-purin-9-yl}-5-(3-methyl-[1,2,4]oxadiazol-5-yl)-tetrahydro-furan-3,4-diol bis(trifluoroacetate).

A solution of Intermediate 2 (0.050 g, 0.08 mmol) in 1,4-dioxane (2 ml) was treated with EEDQ (0.024 g, 0.096 mmol), and N-hydroxy-acetamidine (0.012 g, 0.16 mmol). The resultant mixture was heated at 103° C. with stirring for 6 days. The solution was concentrated in vacuo to afford a yellow oil. A cooled solution of trifluoroacetic acid (0.9 ml) and water (0.1 ml), was added to the yellow oil. The resultant solution was stirred at 0° C. for 6 h, then concentrated in vacuo, and azeotroped with toluene (3X). Purification by preparative HPLC (30–70% acetonitrile in water) gave the title compound as a white solid (0.006 g). LC/MS SYSTEM A R$_t$=3.98 mins, m/z=623 MH$^+$ Example 2

(2R,3R,4S,5S)-2-{6-(2,2-Diphenyl-ethylamino)-2-[2-(1-methyl-1H-imidazol-4-yl)-ethylamino]-purin-9-yl}-5-(3-ethyl-[1,2,4]oxadiazol-5-yl)-tetrahydro-furan-3,4-diol bis(difluoroacetate).

Example 2 was prepared in an analogous manner to Example 1 using N-hydroxy-propionamidine (0.014 g, 0.16 mmol). A solution of Intermediate 2 (0.050 g, 0.08 mmol) in 1,4-dioxan (2 ml) was treated with EEDQ (0.024 g, 0.096 mmol), and N-hydroxy-propionamidine (0.014 g, 0.16 mmol). The resultant mixture was heated at 103° C. with stirring for 6 days. The solution was concentrated in vacuo to afford a yellow oil. A cooled solution of trifluoroacetic acid (0.9 ml) and water (0.1 ml), was added to the yellow oil. The resultant solution was stirred at 0° C. for 6 h, then concentrated in vacuo, and azeotroped with toluene (3X). Purification by preparative HPLC (30–70% acetonitrile in water) gave the title compound as a white solid (0.012 g). LC/MS SYSTEM A R$_t$=4.02 mins, m/z=637 MH$^+$ Example 3

(2R,3R,4S,5S)-2-[6-(2,2-Diphenyl-ethylamino)-2-(pyrrolidin-3R-ylamino)-purin-9-yl]-5-(3-ethyl-[1,2,4]oxadiazol-5-yl)-tetrahydro-furan-3,4-diol formate.

A mixture of Intermediate 4 (0.034 g, 0.062 mmol), (3R)-(+-3-aminopyrrolidine) (0.030 ml, 0.311 mmol) and DMSO (0.03 ml), in a sealed vial (e.g. Reacti-vial™) was heated at 80° C. for 28 h. The resultant crude product was purified by Autoprep. HPLC to afford the title compound after freeze drying as a white solid (0.017 g). LC/MS system A R$_t$=3.65 mins, m/z=598 MH$^+$ Example 4

(2R,3R,4S,5S)-2-[2-(trans-4-Amino-cyclohexylamino)-6-(2,2-diphenyl-ethylamino)-purin-9-yl]-5-(3-ethyl-[1,2,4]oxadiazol-5-yl)-tetrahydro-furan-3,4-diol diformate Example 4 was formed in an analogous manner to Example 3 using trans-1,4,-diaminocyclohexane (0.035 g, 0.311 mmol). The title compound was obtained after freeze-drying as a white solid (0.013 g). LC/MS system B $R_t$=2.58 mins, m/z=626 MH$^+$

Example 5

(2R,3R,4S,5S)-2-[6-(2,2-Diphenyl-ethylamino)-2-(1S-hydroxymethyl-2-methyl-propylamino)-purin-9-yl]-5-(3-ethyl-[1,2,4]oxadiazol-5-yl)-tetrahydro-furan-3,4-diol formate Example 5 was formed in an analogous manner to Example 3 using (S)-2-amino-3-methyl-1-butanol (0.032 g, 0.311 mmol), and heating the reaction mixture for 3 days, at 80–95° C. The title compound was obtained after freeze-drying as a white solid (0.005 g). LC/MS system B $R_t$=3.16 mins, m/z 615 MH$^+$

Example 6

(2R,3R,4S,5S)-2-[6-(1-Ethyl-propylamino)-2-(2-morpholin-4-yl-ethylamino)-purin-9-yl]-5-(3-methyl-[1,2,4]oxadiazol-5-yl)-tetrahydro-furan-3,4-diol formate Intermediate 11 (0.069 g, 0.163 mmol) and 4-(2-aminoethyl)morpholine (0.107 ml, 0.815 mmol) were dissolved in DMSO (0.03 ml) and heated at 80° C. for 26 h in a sealed vial (eg Reacti vial™), a further portion of 4-(2-aminoethyl)morpholine (0.053 ml, 0.407 mmol) was added after the first 20 h. The product was purified by Autoprep. HPLC to give the title compournd after freeze drying as a brown solid (0.059 g). LC/MS system B $R_t$=2.19 min, m/z=517MH$^+$.

Example 7

(2R,3R,4S,5S)-2-{6-Amino-2-[2-(1-methyl-1H-imidazol4-yl)-ethylamino]-purin-9-yl}-5-(3-methyl-[1,2,4]oxadiazol-5-yl)-tetrahydro-furan-3,4-diol bis (trifluoroacetate)

Intermediate 17 (0.048 g), 2-(1-methyl-1H-imidazol-4-yl)ethylamine (0.06 g) in DMSO (0.05 ml) were heated in a sealed vial (eg Reacti vial™) at 90° C. for 20 hrs. The crude material was purified twice by Autoprep HPLC then by preparative HPLC (10–60% Acetonitrile over 22 min), solvent was removed in vacuo and the residue freeze-dried to give the title compound as a brown solid (0.007 g) LC/MS system A $R_t$=1.8 min, m/z 443 (MH$^+$)

Example 8

(2R,3R,4S,5S)-2-[6-Amino-2-(2-pyridin-2-yl-ethylamino)-purin-9-yl]-5-(3-ethyl-[1,2,4]oxadiazol-5-yl)-tetrahydro-furan-3,4-diol diformate Intermediate 18 (0.041 g), 2-(2-aminoethyl)pyridine(0.06 ml), DMSO (0.05 ml), were heated in a sealed vial (eg Reacti vial™) at 90° C. for 16 hrs. The sample was purified by Autoprep HPLC. Solvent was removed in vacuo and the residue freeze-dried to give the title compound as a pale brown solid (0.011 g). LC/MS system B $R_t$=1.92 min, m/z 454 (MH$^+$)

Example 9

(2R,3R,4S,5S)-2-[6-Amino-2-(1S-hydroxymethyl-2-phenyl-ethylamino)-purin-9-yl]-5-(3-ethyl-[1,2,4oxadiazol-5-yl)-tetrahydro-furan-3,4-diol formate Intermediate 18 (0.041 g), (S)-(–)-2-amino-3-phenyl-1-propanol (0.06 g), DMSO (0.05 ml), were heated in a sealed vial (eg Reacti vial™) at 90° C. for 32 hrs, then at 110° C. for 16 hrs. The sample was purified twice by Autoprep. HPLC. Solvent was removed in vacuo and the residue freeze-dried to give the title compound as a white solid (0.003 g). LC/MS system B $R_t$=2.36 min, m/z=483 (MH$^+$)

Example 9

(Alternative Procedure): 2R-[6-Amino-2-(1S-hydroxymethyl-2-phenyl-ethylamino)-purin-yl]-5S-(3-ethyl-[1,2,4]oxadiazol-5-yl)-tetrahydro-furan-3R, 4S-diol formate A mixture of Intermediate 43 (0.160 g, 0.28 mmol) and potassium cyanide (0.009 g, 0.14 mmol) in methanol (3 ml) was stirred at room temperature for 30 min. The solvent was evaporated in vacuo and the residue was purified using to Autoprep. HPLC to furnish the title compound as a white solid (0.050 g). LC/MS SYSTEM C $R_t$=2.35 min, m/z=483 MH$^+$

Example 10

(2R,3R,4S,5S)-2-{6-Amino-2-[2-(1-methyl-1H-imidazol-4-yl)-ethylamino]-purin-9-yl}-5-(3-ethyl-1,2,4]oxadiazol-5-yl)-tetrahydro-furan-3,4-diol diformate Intermediate 18 (0.041 g), 2-(1-methyl-1H-imidazol-4-yl) ethylamine (0.06 g), DMSO (0.05 ml) were heated in a sealed vial (eg Reacti vial™) at 90° C. for 32 hrs, then at 110° C. for 16 hrs. The sample was purified by Autoprep. HPLC, solvent was removed in vacuo and the residue freeze-dried to give the title compound as a brown solid (0.014 g). LC/MS system B $R_t$=1.88 min, m/z=457 (MH$^+$)

Example 11

(2R,3R,4S,5S)-2-(6-Amino-2-cyclopentylamino-purin-9-yl)-5-(3-methyl-[1,2,4]oxadiazol-5-yl)-tetrahydro-furan-3,4-diol formate Intermediate 17 (0.048 g), cyclopentylamine (0.06 ml) in DMSO (0.05 ml) were heated in a sealed vial (eg Reacti vial™) at 90° C. for 20 hrs. The crude material was purified by Autoprep HPLC, solvent was removed in vacuo and the residue freeze-dried to give the title compound as a pale yellow solid (0.006 g) LC/MS system A $R_t$=2.2 min, m/z= 403(MH$^+$)

Example 12

(2R,3R,4S,5S)-2-[6-Amino-2-(1S-hydroxymethyl-2-phenyl-ethylamino)-purin-9-yl]-5-(3-methyl-[1,2,4] oxadiazol-5-yl)-tetrahydro-furan-3,4-diol formate Intermediate 17 (0.048 g), (S)-(–)-2-amino-3-phenyl-1-propanol (0.06 g) in DMSO (0.05 ml) were heated in a sealed vial (eg Reacti vial™) at 90° C. for 20 hrs. The crude material was purified twice by Autoprep HPLC, solvent was removed in vacuo and the residue freeze-dried to give the title compound as a white solid (0.002 g) LC/MS system A $R_t$=2.24 min, m/z=469 (MH$^+$)

Example 13

(2S,3S,4R,5R)-2-(3-Ethyl-[1,2,4]oxadiazol-5-yl)-5-(6-(1-ethyl-propylamino)-2-[2-(1-methyl-1H-imidazol-4-yl)-ethylamino]-purin-9-yl}tetrahydro-furan-3,4-diol formate Intermediate 9 (0.070 g, 0.161 mmol) and 2-(1-methyl-1H-imidazol-4-yl)ethylamine (0.101 g, 0.807 mmol) were dissolved in DMSO (0.03 ml) and heated at 85–100° C. under nitrogen for 8 days, a further portion of 2-(1-methyl-1H-imidazol-4-yl)ethylamine (0.101 g, 0.807 mmol) was added after the first 5 days. The product was purified by Autoprep. HPLC to give the title compound after freeze drying as a cream solid (0.010 g). LC/MS system A $R_t$=3.36 min, m/z=526 MH$^+$.

Example 14

(2R,3R,4S,5S)-2-{6-(1-Ethyl-propylamino)-2-[2-(1-methyl-1H-imidazol-4-yl)-ethylamino]-purin-9-yl}-5-(3-methyl-[1,2,4]oxadiazol-5-yl)-tetrahydro-furan-3,4-diol formate Intermediate 11 (0.069 g, 0.163 mmol) and 2-(1-methyl-1H-imidazol-4-yl)ethylamine (0.102 g, 0.815 mmol) were dissolved in DMSO (0.03 ml) and heated at 85–100° C. under nitrogen for 7 days, a further portion of 2-(1-methyl-1H-imidazol-4-yl)ethylamine (0.102 g, 0.815 mmol) was added after the first 5 days. The product was purified by Autoprep. HPLC to give the title compound after freeze drying as a beige solid (0.013 g). LC/MS system A $R_t$=3.32 min, m/z=512MH$^+$.

Example 15

(2R,3R,4S,5S)-2-(6-Amino-2-phenethylamino-purin-9-yl)-5-(3-methyl-[1,2,4]oxadiazol-5-yl)-tetrahydro-furan-3,4-diol trifluoroacetate Intermediate 21 (0.210 g, 0.44 mmol) was dissolved in trifluoroacetic acid and water 9:1, 2 ml) and the solution was stirred at 20° C. for 3 hrs., and solvent was removed in vacuo. Purification by preparative HPLC (10–90% acetonitrile in water) afforded the title compound after freeze drying as a pale yellow solid (0.088 g). Mass spectrum m/z 439 (MH+ for $C_{20}H_{23}N_8O_4$) Analysis found: C, 46.70; H, 4.05; N, 19.51; $C_{20}H_{22}N_8O_4 \cdot C_2HF_3O_2 \cdot 0.5H_2O$ requires C, 46.54; H, 4.24; N, 19.56

Example 16

(2R,3R,4S,5S)-2-[2-(trans-4-Amino-cyclohexylamino)-6-(1-ethyl-propylamino)-purin-9-yl]-5-(3-methyl-[1,2,4]oxadiazol-5-yl)tetrahydro-furan-3,4-diol formate Intermediate 11 (0.069 g, 0.163 mmol) and trans-1,4-diaminocyclohexane (0.093 g, 0.815 mmol) were dissolved in DMSO (0.03 ml) and heated at 80–90° C. for 66 h in a sealed vial (eg Reacti vial™), a further portion of trans-1,4-diaminocyclohexane (0.093 g, 0.815 mmol) was added after the first 20 h. The product was purified by Autoprep. to give the title compound after freeze drying as a brown solid (0.063 g). LC/MS system B $R_t$=2.12 min, m/z=502 MH$^+$.

Example 17

(2R,3R,4S,5S)-2-[6-(1-Ethyl-propylamino)-2-(1S-hydroxymethyl-2-phenl-ethylamino)-purin-9-yl]-5-(3-methyl-[1,2,4]oxadiazol-5-yl)-tetrahydro-furan-3,4-diol formate Intermediate 11 (0.069 g, 0.163 mmol) and 3-(S)-(−)2-amino-3-phenyl propanol (0.123 g, 0.815 mmol) were dissolved in DMSO (0.03 ml) and heated at 80–95° C. for 5.5 days in a sealed vial (eg Reacti vial™). The product was purified by Autoprep. HPLC to give the title compound after freeze drying as a yellow solid (0.014 g). LC/MS system B $R_t$=2.80 min, m/z=539 MH$^+$.

Example 18

(2R,3R,4S,5S)-2-[6-(1-Ethyl-propylamino)-2-(2-piperidin-1-yl-ethylamino)-purin-9-yl]-5-(3-methyl-[1,2,4]oxadiazol-5-yl)-tetrahydro-furan-3,4-diol formate Intermediate 11 (0.069 g, 0.163 mmol) and 2-piperidinoethylamine (0.116 ml, 0.815 mmol) were dissolved in DMSO (0.03 ml) and heated at 80° C. for 40 h in a sealed vial (Reacti vial™) a further portion of 2-piperidinoethylamine (0.058 ml, 0.407 mmol) was added after the first 20 h. The product was purified by Autoprep. HPLC to give the title compound after freeze drying as a brown solid (0.031 g). LC/MS system B $R_t$=2.25 min, m/z=516 MH$^+$.

Example 19

(2S,3S,4R,5R)-2-(3-Ethyl-[1,2,4]oxadiazol-5-yl)-5-[6-(1-ethyl-propylamino)-2-(2-morpholin-4-yl-ethylamino)-purin-9-yl]-tetrahydro-furan-3,4-diol formate Intermediate 9 (0.070 g, 0.161 mmol) and 4-(2-aminoethyl)morpholine (0.106 ml, 0.807 mmol) were dissolved in DMSO (0.03 ml) and heated at 80° C. in a sealed vial (eg Reacti vial™), for 26 h, a further portion of 4-(2-aminoethyl)morpholine (0.053 ml, 0.403 mmol) was added after the first 6 h. The product was purified by Autoprep. HPLC to give the title compound after freeze drying as a beige solid (0.049 g). LC/MS system B $R_t$=2.27 min, m/z=532 MH$^+$.

Example 20

(2S,3S,4R,5R)-2-(3-Ethyl-[1,2,4]oxadiazol-5-yl)-5-[6-(1-ethyl-propylamino)-2-(2-piperidin-1-yl-ethylamino)-purin-9-yl]-tetrahydro-furan-3,4-diol formate Intermediate 9 (0.070 g, 0.161 mmol) and 2-piperidinoethylamine (0.115 ml, 0.807 mmol) were dissolved in DMSO (0.03 ml) and heated at 80° C. in a sealed vial (eg Reacti vial™), for 40 h, a further portion of 2-piperidinoethylamine (0.057 ml, 0.403 mmol) was added after the first 20 h. The product was purified by Autoprep. HPLC to give the title compound after freeze drying as a brown gum (0.035 g). LC/MS system B $R^t$=2.33 min, m/z=530 MH$^+$.

Example 21

(2S,3S,4R,5R)-2-(3-Ethyl-[1,2,4]oxadiazol-5-yl)-5-[6-(1-ethyl-propylamino)-2-(2-pyridin-2-yl-ethylamino)-purin-9-yl]-tetrahydro-furan-3,4-diol formate Intermediate 9 (0.070 g, 0.161 mmol) and 2-(2-aminoethyl) pyridine (0.096 ml, 0.807 mmol) were dissolved in DMSO (0.03 ml) and heated at 80° C. in a sealed vial (eg Reacti vial™), for 46 h, a further portion of 2-(2-aminoethyl) pyridine (0.096 ml, 0.807 mmol) was added after the first 20 h. The product was purified by Autoprep. HPLC to give the title compound after freeze drying as a beige solid (0.035 g). LC/MS system B $R_t$=2.38 min, m/z=524 MH$^+$.

Example 22

(2R,3R,4S,5S)-2-[2-Cyclopentylamino-6-(1-ethyl-propylamino)-purin-9-yl]-5-3-methyl-[1,2,4] oxadiazol-5-yl)-tetrahydro-furan-3,4-diol formate Intermediate 11 (0.069 g, 0.163 mmol) and cyclopentylamine (0.08 ml, 0.815 mmol) were dissolved in DMSO (0.03 ml) and heated at 80° C. for 20 h in a sealed vial (eg Reacti vial™). The product was purified by Autoprep. HPLC to give the title compound after freeze drying as a beige solid (0.007 g). LC/MS system B $R_t$=2.87 min, m/z=472 MH⁺.

Example 23

(2R,3R,4S,5S)-2-[2-Cyclopentylamino-6-(1-ethyl-propylamino)-purin-9-yl]-5-(3-ethyl-[1,2,4]oxadiazol-5-yl)-tetrahydro-furan-3,4-diol formate Intermediate 9 (0.070 g, 0.161 mmol) and cyclopentylamine (0.08 ml, 0.807 mmol) were dissolved in DMSO (0.03 ml) and heated at 80° C. in a sealed vial (eg Reacti vial™), for 20 h. The product was purified by Autoprep. HPLC to give the title compound after freeze drying as a cream solid (0.008 g). LC/MS system B $R_t$=3.01 min, m/z=486 MH⁺.

Example 24

(2R,3R,4S,5S)-2-[6-(1-Ethyl-propylamino)-2-(2S-hydroxy-cyclopent-(S)-ylamino)-purin-9-yl]-5-(3-methyl-[1,2,4]oxadiazol-5-yl)-tetrahydro-furan-3,4-diol formate Intermediate 11 (0.069 g, 0.163 mmol) and (R,R)-aminocyclopentan-2-ol** (0.082 g, 0.815 mmol) were dissolved in DMSO (0.03 ml) and heated at 80–95° C. for 68 h in a sealed vial (eg Reacti vial™). The product was purified by Autoprep. HPLC to give the title compound after freeze drying as a brown solid (0.005 g). LC/MS system B $R_t$=2.57 min, m/z=489 MH⁺.
** L. E. Overman and S. Sugai, *J. Org. Chem.*, 1985, 50, 4154

Example 25

(2S,3S,4R,5R)-2-(3-Ethyl-[1,2,4]oxadiazol-5-yl)-5-[6-(1-ethyl-propylamino)-2-(2S-hydroxy-cyclopent-(S)-ylamino)-purin-9-yl]-tetrahydro-furan-3,4-diol formate Intermediate 9 (0.070 g, 0.161 mmol) and (R,R)-aminocyclopentan-2-ol** (0.082 g, 0.807 mmol) were dissolved in DMSO (0.03 ml) and heated at 80–95° C. in a sealed vial (eg Reacti vial™), for 68 h. The product was purified by Autoprep. HPLC to give the title compound after freeze drying as a brown solid (0.005 g). LC/MS system B $R_t$=2.68 min, m/z=503 MH⁺.
** L. E. Overman and S. Sugai, J. Org. Chem., 1985, 50, 4154

Example 26

(2R,3R,4S,5S)-2-[6-(1-Ethyl-propylamino)-2-(pyrrolidin-3R-ylamino)-purin-9-yl]-5-(3-methyl-[1,2,4]oxadiazol-5-yl)-tetrahydro-furan-3,4-diol formate Intermediate 11 (0.069 g, 0.163 mmol) and (3R)-(+)-3-aminopyrrolidine (0.070 g, 0.815 mmol) were dissolved in DMSO (0.03 ml) and heated at 80° C. for 6 h in a sealed vial (eg Reacti vial™). The product was purified by Autoprep. HPLC to give the title compound after freeze drying as a cream solid (0.041 g). LC/MS system B $R_t$=2.24 min, m/z=474 MH⁺.

Example 27

(2S,3S,4R,5R)-2-(3-Ethyl-[1,2,4]oxadiazol-5-yl)-5-[6-(1-ethyl-propylamino)-2-(pyrrolidin-3R-ylamino)-purin-9-yl]-tetrahydro-furan-3,4-diol formate Intermediate 9 (0.070 g, 0.161 mmol) and (3R)-(+)-3-aminopyrrolidine (0.07 g, 0.807 mmol) were dissolved in DMSO (0.03 ml) and heated at 80° C. in a sealed vial (eg Reacti vial™), for 6 h. The product was purified by Autoprep. HPLC to give the title compound after freeze drying as a cream solid (0.041 g). LC/MS system B $R_t$=2.31 min, m/z=488 MH⁺.

Example 28

(2R,3R,4S,5S)-2-[6-(1-Ethyl-propylamino)-2-(1S-hydroxymethyl-2-methyl-propylamino)-purin-9-yl]-5-(3-methyl-[1,2,4]oxadiazol-5-yl)-tetrahydro-furan-3,4-diol formate Intermediate 11 (0.069 g, 0.163 mmol) and L-2-amino-3-methylbutanol (0.084 g, 0.815 mmol) were dissolved in DMSO (0.03 ml) and heated at 80–95° C. for 5.5 days in a sealed vial (eg Reacti vial™). The product was purified by Autoprep. HPLC to give the title compound after freeze drying as a yellow gum (0.030 g). LC/MS system B $R_t$=2.59 min, m/z=491 MH⁺.

Example 29

(2R,3R,4S,5S)-2-[2-(trans-4-Amino-cyclohexylamino)-6-(1-ethyl-propylamino)-purin-9-yl]-5-(3-ethyl-[1,2,4]oxadiazol-5-yl)-tetrahydro-furan-3,4-diol formate Intermediate 9 (0.070 g, 0.161 mmol) and trans-1,4-diaminocyclohexane (0.092 g, 0.807 mmol) were dissolved in DMSO (0.03 ml) and heated at 80–90° C. in a sealed vial (eg Reacti vial™), for 66 h, a further portion of trans-1,4-diaminocyclohexane (0.092 mg, 0.807 mmol) was added after the first 20 h. The product was purified by Autoprep. HPLC to give the title compound after freeze drying as a brown solid (0.082 g). LC/MS system B $R_t$=2.21 min, m/z=516 MH⁺.

Example 30

(2R,3R,4S,5S)-2-[6-Amino-2-(2-pyridin-2-yl-ethylamino)-purin-9-yl]-5-(3-methyl-[1,2,4]oxadiazol-5-yl)-tetrahydro-furan-3,4-diol diformate Intermediate 17 (0.048 g), 2-(2-aminoethyl)pyridine (0.06 ml) in DMSO (0.05 ml) were heated in a sealed vial (eg Reacti vial™) at 90° C. for 20 hrs. 2-(2-aminoethyl)pyridine (0.05 ml) was added and the mixture heated at 110° C. for 16 h. Purification by Autoprep. HPLC followed by freeze-drying gave the title compound as a pale brown solid (0.0015 g) LC/MS system B $R_t$=1.88 min, m/z=440 MH⁺.

Example 31

(2R,3R,4S,5S)-2-[6-(2,2-Diphenyl-ethylamino)-2-(2-morpholin-4-yl-ethylamino)-purin-9-yl]-5-(3-ethyl-[1,2,4]oxadiazol-5-yl)-tetrahydro-furan-3,4-diol formate A mixture of Intermediate 4 (0.034 g, 0.062 mmol), 4-(2-aminoethyl)morpholine (0.041 ml, 0.31 mmol) and DMSO (0.03 ml); in a sealed vial (e.g. Reacti-vial™) was heated at 80° C. for 28 h. Purification by Autoprep. HPLC afforded the title compound after freeze drying as a white solid (0.015 g). LC/MS system A $R_t$=3.67 mins, m/z= 642MH⁺

Example 32

(2R,3R,4S,5S)-2-[6-(2,2-Diphenyl-ethylamino)-2-(2-piperidin-1-yl-ethylamino)-purin-9-yl]-5-(3-ethyl-[1,2,4]oxadiazol-5-yl)-tetrahydro-furan-3,4-diol formate A mixture of Intermediate 4 (0.034 g, 0.062 mmol), 2-piperidinoethylamine (0.044 ml, 0.311 mmol) and DMSO (0.03 ml), in a sealed vial (e.g. Reacti-vial™) was heated at 80° C. for 28 h. Purification by Autoprep. HPLC afforded the title compound after freeze drying as a white solid (0.010 g). LC/MS system A $R_t$=3.72 mins, m/z=640MH$^+$

Example 33

(2R,3R,4S,5S)-2-{6-(2,2-Diphenyl-ethylamino)-2-[2-(1-methyl-1H-imidazol-4-yl)-ethylamino]-purin-9-yl}-5-(3-propyl-[1,2,4]oxadiazol-5-yl)-tetrahydro-furan-3,4-diol formate A mixture of Intermediate 23 (0.075 g, 0.135 mmol), and 2-(1-methyl-1H-imidazol-4-yl)ethylamine (0.085 g, 0.677 mmol) in diisopropylethylamine (0.04 ml) and DMSO (0.04 ml), in a sealed vial (e.g. Reacti-vial™) was heated at 85° C. for 40 h. A further portion of 2-(1-methyl-1H-imidazol-4-yl)ethylamine (0.085 g, 0.677 mmol) was added after the first 20 h. Purification by Autoprep. HPLC afforded the title compound after freeze drying as a cream solid (0.037 g). LC/MS system B $R_t$=2.71 mins, m/z=651 MH$^+$

Example 34

(2R,3R,4S,5S)-2-{6-(2,2-Diphenyl-ethylamino)-2-[2-(1H-imidazol-4-yl)-ethylamino]-purin-9-yl}-5-(3-methyl-[1,2,4oxadiazol-5-yl)-tetrahydro-furan-3,4-diol formate A mixture of Intermediate 25 (0.132 g, 0.248 mmol), and histamine (0.138 g, 1.24 mmol) in diisopropylethylamine (0.04 ml) and DMSO (0.04 ml), in a sealed vial (e.g. Reacti-vial™) was heated at 85–90° C. for 40 h. The resultant crude product was purified by Autoprep. HPLC to afford the title compound after freeze drying as a cream solid (0.032 g). LC/MS system B $R_t$=2.59 mins, m/z=609 MH$^+$.

Example 35

(2S,3S,4R,5R)-2-(3-Cyclopropyl-[1,2,4]oxadiazol-5-yl)-5-[6-(1-ethyl-propylamino)-2-(2-piperidin-1-yl-ethylamino)-purin-9-yl]-tetrahydro-furan-3,4-diolldiformate A mixture of Intermediate 27 (70 mg, 0.15 mmol) and 2-piperidinoethylamine (0.117 ml, 0.83 mmol) in dimethylsulphoxide (0.3 ml) in a sealed vial (e.g. Reacti-vial™) was heated with stirring to 90° C. for 4 h. The resultant crude product was purified by Autoprep. HPLC to afford the title compound after freeze-drying as a brown solid (0.015 g) LCMS SYSTEM C $R_t$=2.32 mins m/z=542 MH$^+$

Example 36

(2S,3S,4R,5R)-2-(3-Cyclopropyl-[1,2,4]oxadiazol-5-yl)-5-[6-(1-ethyl-propylamino)-2-(2-morpholin-4-yl-ethylamino)-purin-9-yl]-tetrahydro-furan-3,4-diol diformate Example 36 prepared in an analogous method to Example 35 using 4-(2-aminoethyl)morpholine (0.108 ml, 0.825 mmol) at 90° C. for 4 h. The title compound was afforded after freeze-drying as a brown solid (0.009 g) LCMS SYSTEM C $R_f$=2.32 mins m/z=544 MH$^+$

Example 37

(2S,3S,4R,5R)-2-(3-Cyclopropyl-[1,2,4]oxadiazol-5-yl)-5-[6-(1-ethyl-propylamino)-2-(2-(2-pyridinyl)-ethylamino)-purin-9-yl]-tetrahydro-furan-3,4-diol diformate Example 37 prepared in an analogous manner to Example 35 using 2-(2-aminoethyl)pyridine (0.104 g, 0.825 mmol) at 90° C. for 4 h. The title compound was afforded after freeze-drying as a brown solid (0.012 g) LCMS SYSTEM C $R_t$=2.18 mins m/z=535 MH$^+$

Example 38

(2S,3S,4R,5R)-2-(3-Cyclopropyl-[1,2,4]oxadiazol-5-yl)-5-[6-(1-ethyl-propylamino)-2-(2-(1-methyl-1H-imidazol-4-yl)-ethylamino)-purin-9-yl]-tetrahydro-furan-3,4-diol diformate Example 38 prepared in an analogous method to Example 35 using 2-(1-methyl-1H-imidazol-4-yl)-ethylamine (0.14 g, 0.825 mmol; generated from the corresponding bishydrochloride by neutralization with slight deficient of solid sodium hydroxide in methanol and evaporation of any volatile matters under a jet of nitrogen) at 90° C. for 4 h. The title compound was afforded after freeze-drying as a brown solid (0.015 g) LCMS SYSTEM C $R_t$=2.32 mins m/z=542 MH$^+$

Example 39

(2R,3R,4S,5S)-2-[6-(2,2-Diphenyl-ethylamino)-2-(2-pyrrolidin-1-yl-ethylamino)-purin-9-yl]-5-(3-ethyl-[1,2,4]oxadiazol-5-yl)-tetrahydro-furan-3,4-diol diformate A mixture of Intermediate 3 (70 mg, 0.15 mmol) and 1-(2-aminoethyl)pyrrolidine (0.114 g, 1 mmol) in dimethylsulphoxide (0.2 ml) in a sealed vial (e.g. Reacti-vial™) was heated with stirring to 90° C. for 4 h. The resultant crude product was pufi[]ed by Autoprep. HPLC to afford the title compound after freeze-drying as a brown solid (0.008 g) LCMS SYSTEM B $R_t$=2.67 mins m/z=626 MH$^+$

Example 40

(2R,3R,4S,5S)-2-{6-(2,2-Diphenyl-ethylamino)-2-[2-(pyridin-2-ylamino)-ethylamino]-purin-9-yl}-5-(3-ethyl-[1,2,4]oxadiazol-5-yl)-tetrahydro-furan-3,4-diol diformate Example 40 was prepared in an analogous manner to Example 39 using Intermediate 37 (0.137 g, 1 mmol) at 90° C. for 4 h. The title compound was afforded after freeze-drying as a brown solid (0.003 g) LCMS SYSTEM A $R_t$=2.74 mins m/z=649 MH$^+$

Example 41

(2R,3R,4S,5S)-2-{2-(Bicyclo[2.2.1]hept-2-ylamino)-6-(2,2-diphenyl-ethylamino)-purin-9-yl}-5-(3-ethyl-[1,2,4]oxadiazol-5-yl)-tetrahydro-furan-3,4-diol formate Example 41 was prepared in an analogous manner to Example 39 using (±)-exo-2-aminonorbornane (0.110 g, 1 mmol) at 90° C. for 4 h. The title compound was afforded after freeze-drying as a brown solid (0.008 g) LCMS SYSTEM B $R_t$=3.77 mins m/z=623 MH$^+$

Example 42

(2R,3R,4S,5S)-2-{2-(2-[3,4-Dimethoxy-phenyl]-ethylamino)-6-(2,2-diphenyl-ethylamino)-purin-9-yl}-5-(3-ethyl-[1,2,4]oxadiazol-5-yl)-tetrahydro-furan-3,4-diol formate Example 42 was prepared in an analogous manner to Example 39 using 2-(3,4-dimethoxyphenyl)-ethylamine (0.181, 1 mmol) at 90° C. for 4 h. The title compound was afforded after freeze-drying as a brown solid (0.002 g) LCMS SYSTEM B R$_t$=3.42 mins m/z=693 MH$^+$

Example 43

(2R,3R,4S,5S)-2-[6-(2,2-Diphenyl-ethylamino)-2-(2-hydroxy-ethylamino)-purin-9-yl]-5-(3-ethyl-[1,2,4]oxadiazol-5-yl)-tetrahydro-furan-3,4-diol formate Example 39 was prepared in an analogous manner to Example 39 using 2-hydroxy-ethylamine (0.061 g, 1 mmol) at 90° C. for 4 h. The title compound was afforded after freeze-drying as a brown solid (0.013 g) LCMS SYSTEM B R$_t$=3.02 mins m/z=573 MH$^+$

Example 44

(2R,3R,4S,5S)-2-[6-(2,2-Diphenyl-ethylamino)-2-(4-fluoro-phenylamino)-purin-9-yl]-5-(3-ethyl-[1,2,4]oxadiazol-5-yl)-tetrahydro-furan-3,4-diol formate A mixture of Intermediate 3 (50 mg, 0.09 mmol) and 4-fluoroaniline (0.11 g, 1 mmol) in DMSO (0.2 ml) in a sealed vial (e.g. Reacti-vial™) was heated with stirring to 90° C. for 20 h. and heated for another 20 h. at 110° C. The resultant crude product was purified by Autoprep. HPLC to afford the title compound after freeze-drying as a brown solid (0.005 g) LCMS SYSTEM C Rt=3.60 min m/z=623 MH$^+$

Example 45

(2R,3R,4S,5S)-2-[2-(1-Benzyl-pyrrolidin-3S-ylamino)-6-(2,2-diphenyl-ethylamino)-purin-9-yl]-5-(3-ethyl-[1,2,4]oxadiazol-5-yl)-tetrahydro-furan-3,4-diol diformate Example 45 was prepared in an analogous manner to Example 35 using 1-benzyl-3S-amino-pyrrolidine(0.18 g, 1 mmol) at 90° C. for 20 h. The title compound was afforded after freeze-drying as a brown solid (0.003 g) LCMS SYSTEM C Rt=2.75 min m/z=688 MH$^+$

Example 46

(2R,3R,4S,5S)-2-{6-phenethylamino-2-[2-(1-methyl-1H-imidazol-4-yl)-ethylamino]-purin-9-yl}-5-(3-ethyl-[1,2,4]oxadiazol-5-yl)-tetrahydro-furan-3,4-diol diformate Intermediate 34 (0.083 mg, 0.15 mmol) was dissolved in DCM/THF (9:1, 3 ml) using sonication by ultrasound. N,N-diisopropylethylamine (0.057 ml, 3.32 mmol) and trimethylacetyl chloride (0.021 ml, 0.16 mmol) were added at 0° C. with stirring under nitrogen. The reaction was allowed to warm to room temperature over 2 h, cooled again to 0° C. and N-hydroxy-propionamidine (0.015 g, 0.18 mmol in 0.5 ml tetrahydrofuran) added with stirring. The reaction was allowed to warm to room temperature and stirred for 16 h. The solvents were evaporated in vacuo and the reaction mixture dissolved in toluene (10 ml). The reaction was heated to reflux (120° C.) for 8 h. The product was purified on a Varian Mega Bond Elut cartridge (5 g Si, 20 ml size) eluting with ethyl acetate/methanol (50:1–1:1) to afford crude product as a yellow oil (0.01 g). The product dissolved in trifluoroacetic acid/water (4 ml, 9:1) at 0° C. with stirring under nitrogen for 4 h. The solvents were evaporated in vacuo, azeotroped with toluene (2×50 ml) and purification using Autoprep. HPLC afforded title compound as yellow gum (0.004 g) LCMS SYSTEM C Rt=2.39 min m/z=561 MH$^+$

Example 47

(2R,3R,4S,5S)-2-{6-(2-cyclohexylethylamino)-2-[2-(1-methyl-1H-imidazol4-yl)ethylamino]-purin-9-yl}-5-(3-ethyl-[1,2,4]oxadiazol-5-yl)-tetrahydro-furan-3,4-diol diformate Example 47 was prepared in an analogous manner to Example 46 using Intermediate 35 (0.081 g, 0.146 mmol), trimethylacetyl chloride (0.02 ml, 0.16 mmol), N,N-diisopropylethylamine (0.056 ml, 0.32 mmol) in DCM/THF (9:1, 2 ml) and N-hydroxy-propionamidine (0.014 g, 0.175 mmol). Purification using Autoprep. HPLC afforded title compound as yellow gum (0.003 g) LCMS SYSTEM C Rt=2.54 min m/z=567 MH$^+$

Example 48

(2R,3R,4S,5S)-2-{6-(3,3-Dimethyl-butylamino)-2-[2-(1-methyl-1H-imidazol-4-yl)-ethylamino]-purin-9-yl}-5-(3-ethyl-[1,2,4]oxadiazol-5-yl)-tetrahydro-furan-3,4-diol diformate Example 48 was prepared in an analogous manner to Example 46 using Intermediate 36 (0.05 g, 0.09 mmol), trimethylacetyl chloride (0.012 ml, 0.1 mmol), N,N-diisopropylethylamine (0.035 ml, 0.2 mmol) in DCM/THF (9:1, 2 ml) and N-hydroxy-propionamidine (0.0087 g, 0.11 mmol). Purification using Autoprep. HPLC afforded title compound as yellow gum (0.002 g) LCMS SYSTEM C Rt=2.42 min m/z=541 MH$^+$ Biological data The compounds of the Examples were tested in screen (1) (agonist activity against receptor sub-types) and the results obtained were as follows:

| Example No. | A2a | A3 | A1 |
|---|---|---|---|
| 1 | 1.19 | >197 | 1306 |
| 2 | 0.64 | >197 | 1823 |
| 3* | 4.63 | >304 | 6719 |
| 4 | 5.37 | >383 | >=3996 |
| 5 | 6.12 | >309 | 1391.2 |
| 6* | 41.35 | >642 | >4833 |
| 7* | 11.02 | >117 | 1013.4 |
| 8* | 14.05 | >215 | >=3865 |
| 9* | 0.81 | >231 | 1692.4 |
| 9** | 0.086 | >287 | 3006 |
| 10* | 7.66 | >269 | 3449.6 |
| 11* | 6.66 | >266 | 145.5 |
| 12* | 4.54 | >302 | 1863.5 |
| 13 | 0.61 | >289 | >=4370 |
| 14 | 0.66 | >239 | >4587 |
| 15 | 2.29 | >130 | >5511 |
| 16* | 11.87 | >362 | >6244 |
| 17* | 3.97 | >362 | >6244 |
| 18* | 8.16 | >314 | >6244 |
| 19* | 34.52 | >694 | >5860 |
| 20* | 17.08 | >694 | >=1853 |
| 21* | 9.39 | >303 | >5090 |
| 22 | 22.25 | >193 | 78.28 |
| 23 | 12.72 | >163 | 17.02 |
| 24 | 18.13 | >284 | >5264 |
| 25 | 19.35 | >163 | 515.35 |
| 26* | 5.18 | >284 | >5264 |
| 27* | 10.5 | >284 | 263.14 |
| 28* | 5.49 | >284 | >5263 |
| 29* | 8.92 | >117 | 989.5 |
| 30* | 19.54 | >215 | 1460.7 |
| 31 | 30.6 | >262 | 6452 |
| 32 | 31.4 | >258 | 7521 |
| 33* | 8.35 | >259 | ≧815.9 |

-continued

| Example No. | A2a | A3 | A1 |
|---|---|---|---|
| 34* | 8.31 | 231.1 | 3270.8 |
| 35 | 7.89 | >194 | 912.1 |
| 36 | 20.13 | >194 | >9364 |
| 37 | 49.45 | >87 | >10402 |
| 38 | 2.02 | >87 | 670.04 |
| 39 | 30.21 | >130 | 4505.4 |
| 40 | 4.89 | >130 | >=3311.7 |
| 41 | 23.93 | >130 | 2033.2 |
| 42 | 32.77 | >130 | >6064 |
| 43 | 6.85 | >130 | 1367.6 |
| 44 | 94.39 | >165 | >6131 |
| 45 | 29.82 | >165 | >3738.84 |
| 46 | 0.90 | >165 | 3560.13 |
| 47 | 6.93 | >165 | 4993.28 |
| 48 | 4.40 | >165 | 16.84 |

*Data are minimum values since preparation was found, after testing, to contain an inactive impurity.
**Data on retested purified compound.

Values given in the Table are $EC_{50}$ values as a ratio of that of NECA.

| ABBREVIATIONS | |
|---|---|
| TMS | trimethylsilyl |
| TFA | trifluoroacetic acid |
| DMF | N,N-dimethylformamide |
| NECA | N-ethylcarboxamideadenosine |
| DMAP | 4-dimethylaminopyridine |
| TEMPO | 2,2,6,6-tetramethyl-1-piperidinyloxy, free radical |
| TMSOTf | Trimethylsilyltrifluoromethylsulphonate |
| DBU | 1,8-diazabicyclo[5.4.0]undec-7-ene |
| BSA | bistrimethylsilylacetamide |
| DCM | dichloromethane |
| DAST | diethylaminosulphur trifluoride |
| Ph | phenyl |
| CDI | carbonyldiimidazole |
| EEDQ | 2-ethoxy-1-ethoxycarbonyl-1,2 dihydroquinone |
| NSAID | non-steroidal antiinflammatory drug |
| DMSO | dimethylsulphoxide |
| Me | methyl |
| Et | ethyl |
| THF | tetrahydrofuran |

What is claimed is:

1. A compound of formula (I):

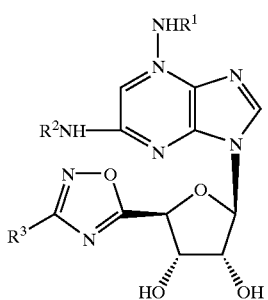

(I)

wherein $R^1$ and $R^2$ independently represent a group selected from:
(i) $C_{3-8}$cycloalkyl-;
(ii) hydrogen;
(iii) aryl$_2$CHCH$_2$—;
(iv) $C_{3-8}$cycloalkylC$_{1-6}$alkyl-;
(v) $C_{1-8}$alkyl-;
(vi) arylC$_{1-6}$alkyl-;
(vii) $R^4R^5$N—C$_{1-6}$alkyl-;
(viii) C$_{1-6}$alkyl-CH(CH$_2$OH)—;
(ix) arylC$_{1-5}$alkyl-CH(CH$_2$OH)—;
(x) arylC$_{1-5}$alkyl-C(CH$_2$OH)$_2$—;
(xi) $C_{3-8}$cycloalkyl independently substituted by one or more —(CH$_2$)$_p$R$^6$ groups;
(xii) H$_2$NC(=NH)NHC$_{1-6}$alkyl-;
(xiii) a group of formula

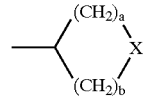

or such a group in which one methylene carbon atom adjacent to X, or both if such exist, is substituted by methyl;
(xiv) —C$_{1-6}$alkyl-OH;
(xv) —C$_{1-8}$haloalkyl;
(xvi) a group of formula

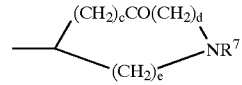

(xvii) aryl; and
(xviii) —(CH$_2$)$_f$SO$_2$NH$_g$(C$_{1-4}$alkyl-)$_{2-g}$ or —(CH$_2$)$_f$SO$_2$NH$_g$(arylC$_{1-4}$alkyl-)$_{2-g}$;

$R^3$ represents methyl, ethyl, —CH=CH$_2$, n-propyl, —CH$_2$CH=CH$_2$, —CH=CHCH$_3$, isopropenyl, cyclopropyl, cyclopropenyl, —CH(OH)CH$_3$, —(CH$_2$)$_q$halogen, —(CH$_2$)$_h$Y(CH$_2$)$_i$H, —COO(CH$_2$)$_l$H, —CON(CH$_2$)$_m$H((CH$_2$)$_n$H), —CO(CH$_2$)$_o$H, or —C((CH$_2$)$_u$H)=NO(CH$_2$)$_v$H;

Y represents O, S or N(CH$_2$)$_j$H;

a and b independently represent an integer 0 to 4 provided that a+b is in the range 3 to 5;

c, d and e independently represent an integer 0 to 3 provided that c+d+e is in the range 2 to 3;

f represents 2 or 3 and g represents an integer 0 to 2;

p represents 0 or 1;

q represents 1 or 2;

h represents 1 or 2 and i represents an integer 0 to 1; such that h+i is in the range 1 to 2;

i represents an integer 0 to 1 such that h+i+j is in the range 1 to 2;

l represents 1 or 2;

m and n independently represent an integer 0 to 2 such that m+n is in the range 0 to 2;

o represents an integer 0 to 2;

u and v independently represent 0 or 1 such that u+v is in the range 0 to 1;

$R^4$ and $R^5$ independently represent hydrogen, C$_{1-6}$alkyl, aryl or aryl-(C$_{1-6}$)alkyl; or NR$^4$R$^5$ together may represent pyridinyl, pyrrolidinyl, piperidinyl, morpholinyl, azetidinyl, azepinyl, piperazinyl or N—C$_{1-6}$alkylpiperazinyl;

$R^6$ represents OH, NH$_2$, NHCOCH$_3$ or halogen;

$R^7$ represents hydrogen, C$_{1-6}$alkyl, —C$_{1-6}$alkylaryl or —COC$_{1-6}$alkyl;

X represents NR$^7$, O, S, SO or SO$_2$;

and salts and solvates thereof.

2. The compound of formula (I) according to claim 1 wherein $R^3$ represents methyl, ethyl, n-propyl, cyclopropyl or —CH$_2$OH.

3. The compound of formula (I) according to claim 2 wherein $R^3$ represents methyl, ethyl or n-propyl.

4. The compound of formula (I) according to claim 2 wherein $R^3$ represents ethyl.

5. The compound of formula (I) according to claim 1 wherein $R^1$ and $R^2$ do not both represent hydrogen.

6. The compound of formula (I) according to claim 1 wherein $R^1$ represents $C_{1-8}$alkyl, $C_{3-8}$cycloalkyl$C_{1-6}$alkyl-, aryl$C_{1-6}$alkyl- or hydrogen.

7. The compound of formula (I) according to claim 1 wherein $R^1$ represents aryl$_2$CHCH$_2$—.

8. The compound of formula (I) according to claim 6 wherein $R^1$ represents —CH(CH$_2$CH$_3$)$_2$, phenylethyl, cyclohexylethyl, —(CH$_2$)$_2$C(CH$_3$)$_3$ or hydrogen.

9. The compound of formula (I) according to claim 1 wherein $R^1$ represents Ph$_2$CHCH$_2$—, —CH(CH$_2$CH$_3$)$_2$, hydrogen or phenylethyl-.

10. The compound of formula (I) according to claim 7 wherein $R^1$ represents Ph$_2$CHCH$_2$—.

11. The compound of formula (I) according to claim 1 wherein $R^2$ represents —CH(CH$_2$OH)C$_{1-3}$alkyl, 4-aminocyclohexyl, pyrrolidinyl or arylCH$_2$CH$_2$—.

12. The compound of formula (I) according to claim 1 wherein $R^2$ represents pyrrolidin-3-yl N-substituted by $C_{1-6}$alkyl or benzyl, $R^4R^5NC_{1-6}$alkyl, $C_{1-6}$alkyl-OH, aryl, aryl$C_{1-5}$alkyl-CH(CH$_2$OH)—, $C_{3-8}$cycloalkyl, aryl(CH$_2$)$_2$— or $C_{3-8}$cycloalkyl independently substituted by one or more —(CH$_2$)$_p$R$^6$ groups.

13. The compound of formula (I) according to claim 12 wherein $R^2$ represents 2-(1H-imidazol-4-yl) ethyl, morpholin-1-ylethyl, pyrrolidin-1-ylethyl, pyridin-2-ylaminoethyl, (+)-exonorborn-2-yl, 3,4-dimethoxy phenylethyl, 2-hydroxyethyl, 4-fluorophenyl, N-benzyl-pyrrolidin-3-yl, pyridin-2ylethyl, 1S-hydroxymethyl-2-phenyl-ethyl, cyclopentyl, phenylethyl, piperidin-1-ylethyl or 2-hydroxypentyl.

14. The compound of formula (I) according to claim 11 wherein $R^2$ represents —CH(CH$_2$OH)CH(CH$_3$)$_2$, trans-4-amino-cyclohexyl, 2-(1-methyl-1H-imidazol-4-yl)CH$_2$CH$_2$— or pyrrolidin-3-yl.

15. The compound of formula (I) according to claim 1 wherein $R^2$ represents 2-(1-methyl-1H-imidazol-4-yl) CH$_2$CH$_2$—, 1S-hydroxymethyl-2-phenylethyl, phenylethyl or 1S-hydroxymethyl-2-methyl-propyl.

16. The compound of formula (I) according to claim 1 wherein $R^4$ and $R^5$ independently represent hydrogen, $C_{1-6}$alkyl, aryl or aryl-(C$_{1-6}$)alkyl; or NR$^4$R$^5$ together represent pyrrolidinyl, piperidinyl, morpholinyl, azetidinyl, azepinyl, piperazinyl or N—C$_{1-6}$alkylpiperazinyl.

17. The compound of formula (I) according to claim 16 wherein $R^4$ and $R^5$ independently represent hydrogen or aryl; or NR$^4$R$^5$ together represent pyrrolidinyl, piperidinyl, morpholinyl, azetidinyl, azepinyl, piperazinyl or N-methylpiperazinyl.

18. The compound of formula (I) according to claim 1 which is (2R,3R,4S,5S)-2-{6-(2,2-Diphenyl-ethylamino)-2-[2-(1-methyl-1H-imidazol-4-yl)-ethylamino]-purin-9-yl}-5-(3-ethyl-[1,2,4]oxadiazol-5-yl)-tetrahydro-furan-3,4-diol or a salt or solvate thereof.

19. The compound of formula (I) according to claim 1 which is (2R,3R,4S,5S)-2-[6-Amino-2-(1S-hydroxymethyl-2-phenyl-ethylamino)-purin-9-yl]-5-(3-ethyl-[1,2,4] oxadiazol-5-yl)-tetrahydro-furan-3,4-diol or a salt or solvate thereof.

20. The compound of formula (I) according to claim 1 which is (2R,3R,4S,5S)-2-{6-(2,2-Diphenyl-ethylamino)-2-[2-(1-methyl-1H-imidazol-4-yl)-ethylamino]-purin-9-yl}-5-(3-methyl-[1,2,4]oxadiazol-5-yl)-tetrahydro-furan-3,4-diol;

(2R,3R,4S,5S)-2-[6-(2,2-Diphenyl-ethylamino)-2-(pyrrolidin-3R-ylamino)-purin-9-yl]-5-(3-ethyl-[1,2,4] oxadiazol-5-yl)-tetrahydro-furan-3,4-diol;

(2R,3R,4S,5S)-2-[2-(trans-4-Amino-cyclohexylamino)-6-(2,2-diphenyl-ethylamino)-purin-9-yl]-5-(3-ethyl-[1,2,4]oxadiazol-5-yl)-tetrahydro-furan-3,4-diol;

(2R,3R,4S,5S)-2-[6-(2,2-Diphenyl-ethylamino)-2-(1S-hydroxymethyl-2-methyl-propylamino)-purin-9-yl]-5-(3-ethyl-[1,2,4]oxadiazol-5-yl)-tetrahydro-furan-3,4-diol;

(2R,3R,4S,5S)-2-[6-(1-Ethyl-propylamino)-2-(2-morpholin-4-yl-ethylamino)-purin-9-yl]-5-(3-methyl-[1,2,4]oxadiazol-5-yl)-tetrahydro-furan-3,4-diol;

(2R,3R,4S,5S)-2-{6-Amino-2-[2-(1-methyl-1H-imidazol-4-yl)-ethylamino]-purin-9-yl}-5-(3-methyl-[1,2,4]oxadiazol-5-yl)-tetrahydro-furan-3,4-diol;

(2R,3R,4S,5S)-2-[6-Amino-2-(2-pyridin-2-yl-ethylamino)-purin-9-yl]-5-(3-ethyl-[1,2,4]oxadiazol-5-yl)-tetrahydro-furan-3,4-diol;

(2R,3R,4S,5S)-2-{6-Amino-2-[2-(1-methyl-1H-imidazol-4-yl)-ethylamino]-purin-9-yl}-5-(3-ethyl-[1,2,4]oxadiazol-5-yl)-tetrahydro-furan-3,4-diol;

(2R,3R,4S,5S)-2-(6-Amino-2-cyclopentylamino-purin-9-yl)-5-(3-methyl-[1,2,4]oxadiazol-5-yl)-tetrahydro-furan-3,4-diol;

(2R,3R,4S,5S)-2-[6-Amino-2-(1S-hydroxymethyl-2-phenyl-ethylamino)-purin-9-yl]-5-(3-methyl-[1,2,4] oxadiazol-5-yl)-tetrahydro-furan-3,4-diol;

(2S,3S,4R,5R)-2-(3-Ethyl-[1,2,4]oxadiazol-5-yl)-5-{6-(1-ethyl-propylamino)-2-[2-(1-methyl-1H-imidazol-4-yl)-ethylamino]-purin-9-yl}-tetrahydro-furan-3,4-diol;

(2R,3R,4S,5S)-2-{6-(1-Ethyl-propylamino)-2-[2-(1-methyl-1H-imidazol-4-yl)-ethylamino]-purin-9-yl}-5-(3-methyl-[1,2,4]oxadiazol-5-yl)-tetrahydro-furan-3,4-diol;

(2R,3R,4S,5S)-2-(6-Amino-2-phenethylamino-purin-9-yl)-5-(3-methyl-[1,2,4]oxadiazol-5-yl)-tetrahydro-furan-3,4-diol;

(2R,3R,4S,5S)-2-[2-(trans-4-Amino-cyclohexylamino)-6-(1-ethyl-propylamino)-purin-9-yl]-5-(3-methyl-[1,2,4]oxadiazol-5-yl)-tetrahydro-furan-3,4-diol;

(2R,3R,4S,5S)-2-[6-(1-Ethyl-propylamino)-2-(1S-hydroxymethyl-2-phenyl-ethylamino)-purin-9-yl]-5-(3-methyl-[1,2,4]oxadiazol-5-yl)-tetrahydro-furan-3,4-diol;

(2R,3R,4S,5S)-2-[6-(1-Ethyl-propylamino)-2-(2-piperidin-1-yl-ethylamino)-purin-9-yl]-5-(3-methyl-[1,2,4]oxadiazol-5-yl)-tetrahydro-furan-3,4-diol;

(2S,3S,4R,5R)-2-(3-Ethyl-[1,2,4]oxadiazol-5-yl)-5-[6-(1-ethyl-propylamino)-2-(2-morpholin-4-yl-ethylamino)-purin-9-yl]-tetrahydro-furan-3,4-diol;

(2S,3S,4R,5R)-2-(3-Ethyl-[1,2,4]oxadiazol-5-yl)-5-[6-(1-ethyl-propylamino)-2-(2-piperidin-1-yl-ethylamino)-purin-9-yl]-tetrahydro-furan-3,4-diol;

(2S,3S,4R,5R)-2-(3-Ethyl-[1,2,4]oxadiazol-5-yl)-5-[6-(1-ethyl-propylamino)-2-(2-pyridin-2-yl-ethylamino)-purin-9-yl]-tetrahydro-furan-3,4-diol;

(2R,3R,4S,5S)-2-[2-Cyclopentylamino-6-(1-ethyl-propylamino)-purin-9-yl]-5-(3-methyl-[1,2,4] oxadiazol-5-yl)-tetrahydro-furan-3,4-diol;

(2R,3R,4S,5S)-2-Cyclopentylamino-6-(1-ethyl-propylamino)-purin-9-yl]-5-(3-ethyl-[1,2,4]oxadiazol-5-yl)-tetrahydro-furan-3,4-diol;

(2R,3R,4S,5S)-2-[6-(1-Ethyl-propylamino)-2-(2S-hydroxy-cyclopent-(S)-ylamino)-purin-9-yl]-5-(3-methyl-[1,2,4]oxadiazol-5-yl)-tetrahydro-furan-3,4-diol;

(2S,3S,4R,5R)-2-(3-Ethyl-[1,2,4]oxadiazol-5-yl)-5-[6-(1-ethyl-propylamino)-2-(2S-hydroxy-cyclopent-(S)-ylamino)-purin-9-yl]-tetrahydro-furan-3,4-diol;

(2R,3R,4S,5S)-2-[6-(1-Ethyl-propylamino)-2-(pyrrolidin-3R-ylamino)-purin-9-yl]-5-(3-methyl-[1,2,4]oxadiazol-5-yl)-tetrahydro-furan-3,4-diol;

(2S,3S,4R,5R)-2-(3-Ethyl-[1,2,4]oxadiazol-5-yl)-5-[6-(1-ethyl-prnpylamino)-2-(pyrrolidin-3R-ylamino)-purin-9yl]-tetrahydro-furan-3,4-diol;

(2R,3R,4S,5S)-2-[6-(1-Ethyl-propylamino)-2-(1S-hydroxymethyl-2-methyl-propylamino)-purin-9-yl]-5-(3-methyl-[1,2,4]oxadiazol-5-yl)-tetrahydro-furan-3,4-diol;

(2R,3R,4S,5S)-2-[2-(trans-4-Amino-cyclohexylamino)-6-(1-ethyl-propylamino)-purin-9-yl]-5-(3-ethyl-[1,2,4]oxadiazol-5-yl)-tetrahydro-furan-3,4-diol;

(2R,3R,4S,5S)-2-[6-Amino-2-(2-pyridin-2-yl-ethylamino)-purin-9-yl]-5-(3-methyl-[1,2,4]oxadiazol-5-yl)-tetrahydro-furan-3,4-diol;

(2R,3R,4S,5S)-2-[6-(2,2-Diphenyl-ethylamino)-2-(2-morpholin-4-yl-ethylamino)-purin-9-yl]-5-(3-ethyl-[1,2,4]oxadiazol-5-yl)-tetrahydro-furan-3,4-diol;

(2R,3R,4S,5S)-2-[6-(2,2-Diphenyl-ethylamino)-2-(2-piperidin-1-yl-ethylamino)-purin-9-yl]-5-(3-ethyl-[1,2,4]oxadiazol-5-yl)-tetrahydro-furan-3,4-diol;

(2R,3R,4S,5S)-2-{6-(2,2-Diphenyl-ethylamino)-2-[2-(1-methyl-1H-imidazol-4-yl)-ethylamino]-purin-9-yl}-5-(3-propyl-[1,2,4]oxadiazol-5-yl)-tetrahydro-furan-3,4-diol;

(2R,3R,4S,5S)-2-{6-(2,2-Diphenyl-ethylamino)-2-[2-(1H-imidazol-4-yl)-ethylamino]-purin-9-yl}-5-(3-methyl-[1,2,4]oxadiazol-5-yl)-tetrahydro-furan-3,4-diol;

(2S,3S,4R,5R)-2-(3-Cyclopropyl-[1,2,4]oxadiazol-5-yl)-5-[6-(1-ethyl-propylamino)-2-(2-piperidin-1-yl-ethylamino)-purin-9-yl]-tetrahydro-furan-3,4-diol;

(2S,3S,4R,5R)-2-(3-Cyclopropyl-[1,2,4]oxadiazol-5-yl)-5-[6-(1-ethyl-propylamino)-2-(2-morpholin-4-yl-ethylamino)-purin-9-yl]-tetrahydro-furan-3,4-diol;

(2S,3S,4R,5R)-2-(3-Cyclopropyl-[1,2,4]oxadiazol-5-yl)-5-[6-(1-ethyl-propylamino)-2-(2-(2-pyridinyl)-ethylamino)-purin-9-yl]-tetrahydro-furan-3,4-diol;

(2S,3S,4R,5R)-2-(3-Cyclopropyl-[1,2,4]oxadiazol-5-yl)-5-[6-(1-ethyl-propylamino)-2-(2-(1-methyl-1H-imidazol-4-yl)-ethylamino)-purin-9-yl]-tetrahydro-furan-3,4-diol;

(2R,3R,4S,5S)-2-[6-(2,2-Diphenyl-ethylamino)-2-(2-pyrrolidin-1-yl-ethylamino)-purin-9-yl]-5-(3-ethyl-[1,2,4]oxadiazol-5-yl)-tetrahydro-furan-3,4-diol;

(2R,3R,4S,5S)-2-{6-(2,2-Diphenyl-ethylamino)-2-[2-(pyrdin-2-ylamino)-ethylamino]-purin-9-yl}-5-(3-ethyl-[1,2,4]oxadiazol-5-yl)-tetrahydro-furan-3,4-diol;

(2R,3R,4S,5S)-2-{2-(Bicyclo[2.2.1]hept-2-ylamino)-6-(2,2-diphenyl-ethylamino)-purin-9-yl}-5-(3-ethyl-[1,2,4]oxadiazol-5-yl)-tetrahydro-furan-3,4-diol;

(2R,3R,4S,5S)-2-{2-(2-[3,4-Dimethoxy-phenyl]-ethylamino)-6-(2,2-diphenyl-ethylamino)-purin-9-yl}-5-(3-ethyl-[1,2,4]oxadiazol-5-yl)-tetrahydro-furan-3,4-diol;

(2R,3R,4S,5S)-2-[6-(2,2-Diphenyl-ethylamino)-2-(2-hydroxy-ethylamino)-purin-9-yl]-5-(3-ethyl-[1,2,4]oxadiazol-5-yl)-tetrahydro-furan-3,4-diol;

(2R,3R,4S,5S)-2-[6-(2,2-Diphenyl-ethylamino)-2-(4-fluoro-phenylamino)-purin-9-yl]-5-(3-ethyl-[1,2,4]oxadiazol-5-yl)-tetrahydro-furan-3,4-diol;

(2R,3R,4S,5S)-2-[2-(1-Benzyl-pyrrolidin-3S-ylamino)-6-(2,2-diphenyl-ethylamino)-purin-9-yl]-5-(3-ethyl-[1,2,4]oxadiazol-5yl)-tetrahydro-furan-3,4-diol;

(2R,3R,4S,5S)-2-{6-phenethylamino-2-[2-(1-methyl-1H-imidazol-4-yl)-ethylamino]-purin-9-yl}-5-(3-ethyl-[1,2,4]oxadiazol-5-yl)-tetrahydro-furan-3,4-diol;

(2R,3R,4S,5S)-2-{6-(2-cyclohexylethylamino)-2-[2-(1-methyl-1H-imidazol-4-yl)-ethylamino]-purin-9-yl}-5-(3-ethyl-[1,2,4]oxadiazol-5-yl)-tetrahydro-furan-3,4-diol;

(2R,3R,4S,5S)-2-{6-(3,3-Dimethyl-butylamino)-2-[2-(1-methyl-1H-imidazol-4-yl)-ethylamino]-purin-9-yl}-5-(3-ethyl-[1,2,4]oxadiazol-5-yl)-tetrahydro-furan-3,4-diol;

or a salt or solvate of any one thereof.

21. A pharmaceutical composition comprising a compound of formula (I) as defined in claim 1 or a pharmaceutically acceptable salt or solvate thereof in admixture with one or more pharmaceutically acceptable diluents or carriers.

22. A method of treatment of inflammatory diseases asthma or chronic obstructive pulmonary disease (COPD) which comprises administering to a patient an effective amount of a compound of formula (I) as defined in claim 1 or a pharmaceutically acceptable salt or solvate thereof.

23. A process for preparation of a compound of formula (I) as defined in claim 1 which comprises:

(i) reacting a compound of formula (II)

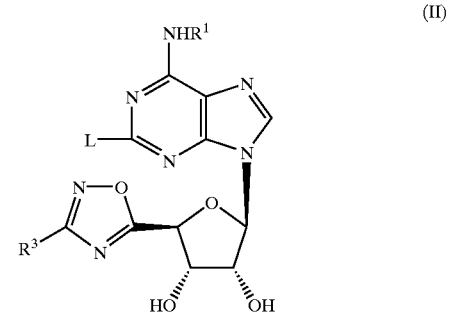

or a protected derivative thereof;

wherein $R^1$ is as defined in claim 1 and $R^3$ is as defined in claim 1 and L is a chlorine or other halogen atom with a compound of formula $R^2NH_2$ or a protected derivative thereof, wherein $R^2$ is as defined in claim 1;

(ii) reacting a compound of formula (VI)

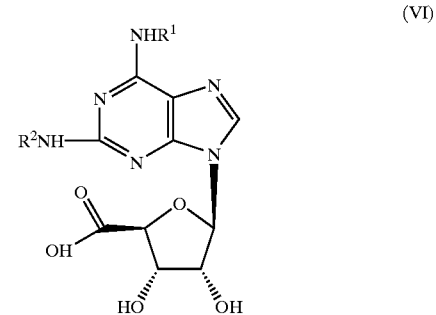

wherein $R^1$ is as defined in claim 1 and $R^2$ is as defined in claim 1 or a protected derivative thereof with a carboxyl activating agent, and an amidoxime compound of formula OH—N=C(R³)NH₂, wherein R³ is as defined in claim 1;

(iii) reacting a compound of formula (IX)

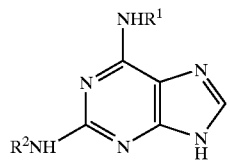
(IX)

wherein R¹ is as defined in claim 1 and R² is as defined in claim 1 with a compound of formula (X)

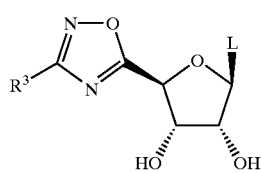
(X)

wherein R³ is as defined in claim 1 and L is a leaving group or a protected derivative thereof; or (iv) deprotecting a protected compound of formula (I)

and where desired or necessary converting a compound of formula (I) or a salt thereof into another salt thereof.

24. A process for preparation of a compound of formula (I) as defined in claim 1 which comprises:

(i) reacting a compound of formula (IIa)

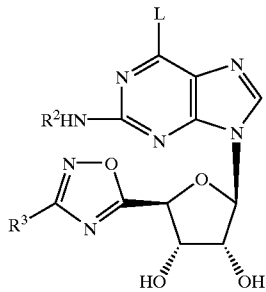
(IIa)

or a protected derivative thereof;

wherein R² is as defined in claim 1 and R³ is as defined in claim 1 and L is a chlorine or other halogen atom with a compound of formula R¹NH₂, wherein R¹ is as defined in claim 1; or (ii) preparing a compound of formula (I) wherein R¹ represents hydrogen by conversion of a compound of formula (IIb)

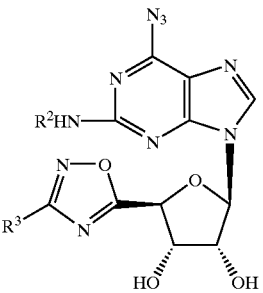
(IIb)

wherein R² is as defined in claim 1 and R³ is as defined in claim 1.

25. A compound of formula (II)

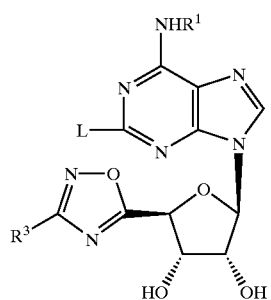
(II)

wherein R¹ is as defined in claim 1 and R³ is as defined in claim 1 and L represents a leaving group, or a protected derivative thereof.

26. A compound of formula (V)

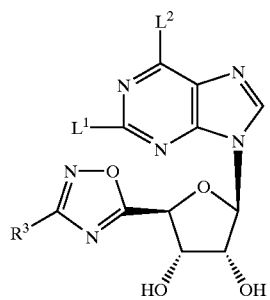
(V)

wherein R³ is as defined in claim 1 and L¹ and L² independently represent a leaving group or a protected derivative thereof.

27. A compound of formula (X)

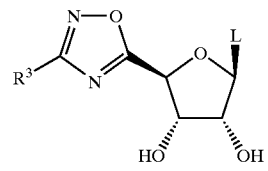
(X)

wherein R³ is as defined in claim 1 and L represents a leaving group, or a protected derivative thereof.

* * * * *